(12) United States Patent
Schaffer et al.

(10) Patent No.: US 11,534,114 B2
(45) Date of Patent: Dec. 27, 2022

(54) 18F LABELED AMINO ACIDS, DERIVATIVES THEREOF AND METHOD OF MAKING SAME

(71) Applicant: SIMON FRASER UNIVERSITY, Burnaby (CA)

(72) Inventors: Paul Schaffer, Burnaby (CA); Hua Yang, Burnaby (CA); Robert Britton, North Vancouver (CA); Matthew Nodwell, Coquitlam (CA); Zheliang Yuan, Burnaby (CA)

(73) Assignee: Simon Fraser University, Burnaby (CA)

( * ) Notice: Subject to any disclaimer, the term of this patent is extended or adjusted under 35 U.S.C. 154(b) by 0 days.

(21) Appl. No.: 16/327,638

(22) PCT Filed: Aug. 23, 2017

(86) PCT No.: PCT/CA2017/050996
§ 371 (c)(1),
(2) Date: Feb. 22, 2019

(87) PCT Pub. No.: WO2018/035610
PCT Pub. Date: Mar. 1, 2018

(65) Prior Publication Data
US 2019/0223814 A1    Jul. 25, 2019

Related U.S. Application Data

(60) Provisional application No. 62/452,999, filed on Feb. 1, 2017, provisional application No. 62/378,349, filed on Aug. 23, 2016.

(51) Int. Cl.
| | |
|---|---|
| *A61B 6/03* | (2006.01) |
| *C07K 5/10* | (2006.01) |
| *A61K 51/08* | (2006.01) |
| *C07K 7/06* | (2006.01) |
| *C07K 5/06* | (2006.01) |
| *C07K 1/13* | (2006.01) |
| *C07K 5/08* | (2006.01) |
| *C07K 5/02* | (2006.01) |
| *C07B 59/00* | (2006.01) |
| *A61K 51/04* | (2006.01) |
| *C07C 275/16* | (2006.01) |
| *C07C 237/12* | (2006.01) |
| *C07C 229/20* | (2006.01) |
| *C07C 229/08* | (2006.01) |
| *C07C 229/26* | (2006.01) |
| *C07C 229/36* | (2006.01) |

(52) U.S. Cl.
CPC .......... *A61B 6/037* (2013.01); *A61K 51/0406* (2013.01); *A61K 51/08* (2013.01); *C07B 59/001* (2013.01); *C07C 229/08* (2013.01); *C07C 229/20* (2013.01); *C07C 229/26* (2013.01); *C07C 229/36* (2013.01); *C07C 237/12* (2013.01); *C07C 275/16* (2013.01); *C07K 1/13* (2013.01); *C07K 5/0217* (2013.01); *C07K 5/06191* (2013.01); *C07K 5/0827* (2013.01); *C07K 5/1027* (2013.01); *C07K 7/06* (2013.01)

(58) Field of Classification Search
CPC ........ A61B 6/037; C07K 5/1027; C07K 7/06; C07K 5/06191; C07K 1/13; C07K 5/0827; C07K 5/0217; A61K 51/08; A61K 51/0406; C07B 59/001; C07C 275/16; C07C 237/12; C07C 229/20; C07C 229/08; C07C 229/26; C07C 229/36
See application file for complete search history.

(56) References Cited

U.S. PATENT DOCUMENTS

2007/0081941 A1* 4/2007 Mertens ............. A61K 49/0438
424/1.11

FOREIGN PATENT DOCUMENTS

| WO | 2003093412 A2 | 11/2003 |
| WO | 2015000076 A1 | 1/2015 |
| WO | 2015134467 A1 | 9/2015 |

OTHER PUBLICATIONS

Extended European Search Report for EP Application No. 17842490.9 dated Mar. 3, 2020.
Bouhlel, et al., "Synthesis, Radiolabeling, and Biological Evaluation of (R)- and (S)-2-Amino-5-[18F]fluoro-2-methylpentanoic Acid ((R)-, (S)-[18F]FAMPe) as Potential Positron Emission Tomography Tracers for Brain Tumors", Journal of Medicinal Chemistry, 2015, 58, 3817-3829.
Bouhlel, et al., "Effect of α-Methyl versus α-Hydrogen Substitution on Brain Availability and Tumor Imaging Properties of Heptanoic [F-18]Fluoroalkyl Amino Acids for Positron Emission Tomography (PET)", Journal of Medicinal Chemistry, 2016, 59, 3515-3531.
International Search Report for PCT/CA2017/050996 dated Nov. 20, 2017.

(Continued)

Primary Examiner — Robert S Cabral
(74) Attorney, Agent, or Firm — Thompson Coburn LLP; William A. Holtz

(57) ABSTRACT

The present invention provides $^{18}$F-labeled amino acids or derivatives thereof having formula (I) and methods of making same, which can be suitable for PET imaging:

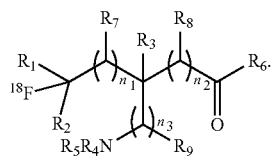

20 Claims, 33 Drawing Sheets

(56) References Cited

OTHER PUBLICATIONS

McConathy, et al., "Synthesis and evaluation of 2-amino-4-[18F]fluoro-2-methylbutanoic acid (FAMB): relationship of amino acid transport to tumor imaging properties of branched fluorinated amino acids", Nuclear Medicine and Biology 30 (2003) 477-490.

Nodwell, et al., "F-Fluorination of Unactivated C—H Bonds in Branched Aliphatic Amino Acids: Direct Synthesis of Oncological Positron Emission Tomography Imaging Agents", Journal of the American Chemical Society 2017, 139, 3595-3598.

Wang, L., et al., "Synthesis and evaluation of 18F labeled alanine derivatives as potential tumor imaging agents", Nuclear Medicine and Biology 39 (2012) 933-943.

Written Opinion of the International Searching Authority for PCT/CA2017/050996 dated Nov. 20, 2017.

Olszewski et al. "NAAG peptidase inhibition reduces locomotor activity and some stereotypes in the PCP model of schizophrenia via group II mGluR" Journal of Neurochemistry, 2004, 89, 876-885.

Padmakshan et al. "Stereocontrolled Synthesis of (S)-g-Fluoroleucine" Synlett, 2007, 1083-1084.

Nagamori et al. "Structure-activity relations of leucine derivatives reveal critical moieties for cellular uptake and activation of mTORC1-mediated signaling" Amino Acids, 2016, 48, 1045-1058.

Examination Report dated Feb. 24, 2021, in respect of corresponding European Patent Application No. 17842490.9.

Examination Report dated Jan. 24, 2022, in respect of corresponding European Patent Application No. 17842490.9.

Chin et al.: "Synthesis and Preliminary Evaluation of 5-[18F]fluoroleucine" Current Radiopharmaceuticals, 2017, 10, 1-9.

Reddy et al.: "Efficient Method for Selective Introduction of Substituents as C(5) of Isoleucine and Other α-Amino Acids" Organic Letters 2006 vol. 8, No. 13 2819-2821.

Table 8.1, Organic Chemistry, Paula Bruice, Fifth Edition, p. 348, 2007 Pearson Prentice Hall.

\* cited by examiner

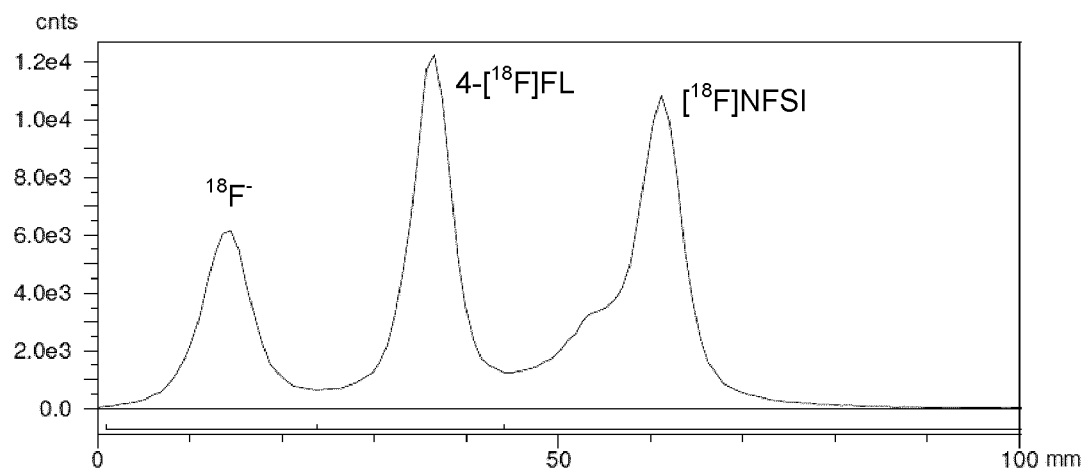
Figure 4
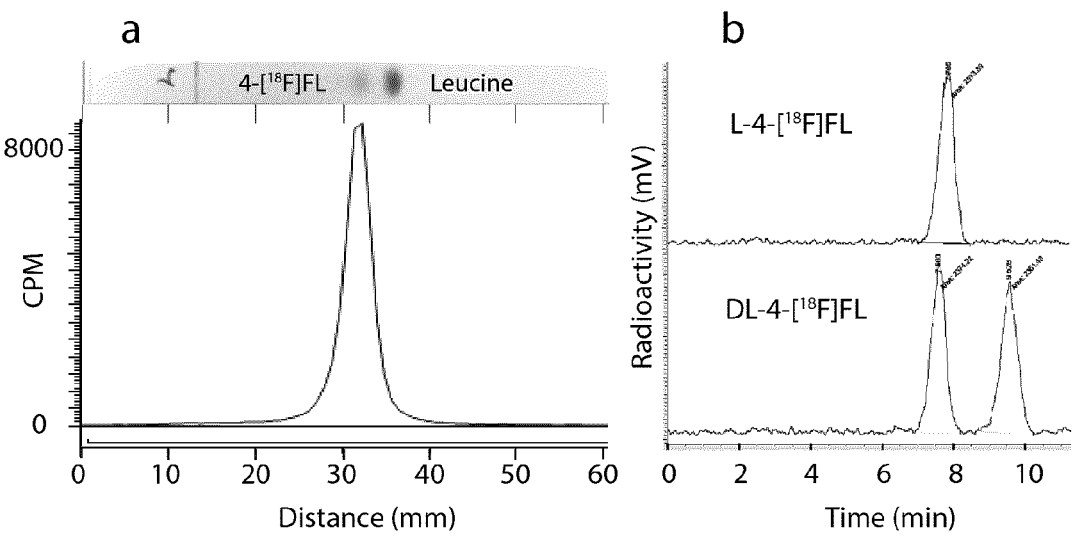
Figure 5a
Figure 5b

18F LABELED AMINO ACIDS, DERIVATIVES THEREOF AND METHOD OF MAKING SAME

CROSS-REFERENCE TO RELATED APPLICATIONS

This is a 35 U.S.C. § 371 U.S. National Phase Application of International Patent Application No. PCT/CA2017/050996 filed on Aug. 23, 2017, which claims the benefit of U.S. Provisional Application Ser. No. 62/378,349 filed Aug. 23, 2016 and U.S. Provisional Application Ser. No. 62/452,999 filed Feb. 1, 2017, all of which are incorporated herein by reference in their entireties.

FIELD OF THE INVENTION

The present invention pertains to the field of fluorinated amino acids, derivative thereof, specifically to $^{18}$F-labeled amino acids or derivatives thereof and process of making same.

BACKGROUND OF THE INVENTION

Molecular imaging has the potential to detect disease progression or therapeutic effectiveness earlier than most conventional methods in the fields of oncology, neurology and cardiology, Several promising molecular imaging technologies, such as optical imaging, MRI, and Positron emission tomography (PET) have been developed. PET is of particular interest for drug development because of its high sensitivity and ability to provide quantitative and kinetic data.

Positron emission tomography (PET) uses radioisotopes to interrogate specific physiological processes in real time and in living systems. PET is therefore ideally suited for the early detection of tumors and metastases, and has become the standard of care in the diagnosis, staging, and treatment planning for various malignancies. The selective imaging of cancers with PET often exploits radiotracers that target aberrant cellular metabolism or increased protein expression. For example, the widely used cancer diagnostic 2-deoxy-2-[$^{18}$F]fluoro-D-glucose (formula 1) takes advantage of the increased glucose uptake and glycolysis in many tumors. Increased amino acid (AA) uptake through over-expression of AA transporters is also a signature feature in cancers, and consequently radiolabeled AAs are highly sought as imaging agents. Radiolabeled AA such as O-(2-[18F]fluoroethyl) tyrosine (2) and [18F]-(2S,4R)-4-fluoro glutamine (3) have also been used as imaging agents.

The uptake of AAs by L-type AA transporters is a particularly appealing pathway to target with PET radiotracers. Most notably, the LAT1 isoform transports branched and aromatic AAs, and is highly upregulated in several cancers (e.g., prostate, breast and brain) and at metastatic sites.

Among the wide range of AAs transported by LAT1, leucine plays a uniquely important role in cancer biology. Large cellular concentrations of this AA are necessary for accelerated protein synthesis and to trigger mTORC1 activation and rapid cell division. L-1-[$^{11}$C]leucine represents a promising PET imaging agent. Unfortunately, the widespread use of this radiotracer is limited by its challenging multi-step radiosynthesis and reliance on the rapidly decaying radionuclide 11C (t½=20.4 min), which restricts use to PET clinics with on-site cyclotron facilities. The more clinically relevant radionuclide 18F (t½=109.8 min) is incorporated in the leucine mimic [$^{18}$F]FACBC (4), which has shown significant potential as a PET imaging agent for prostate cancer. Recently, the boramino acid [$^{18}$F]Leu-BF3 (5) was also reported, adding to the repertoire of radiolabelled leucine mimics.

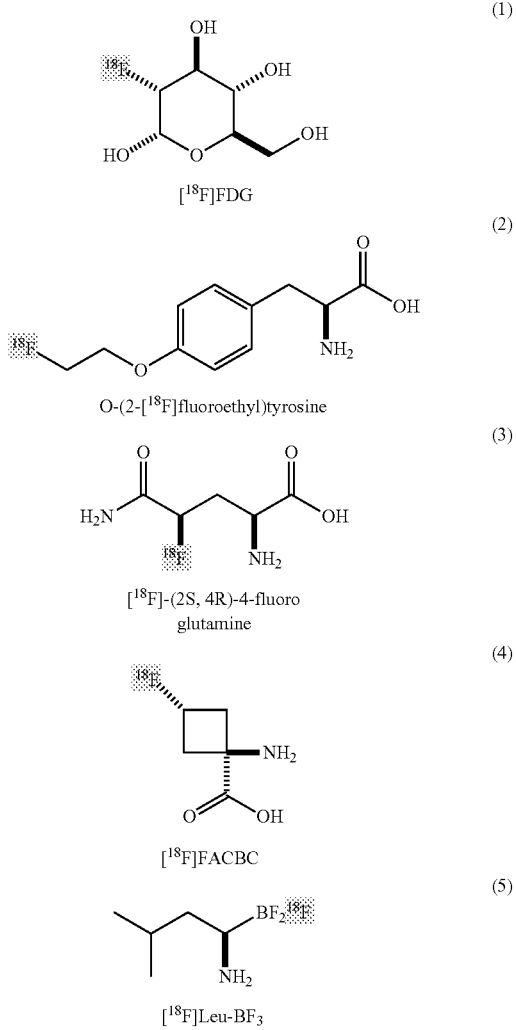

Preparation of radiolabeled amino acids as shown above is a challenge, as the synthesis processes require significant alteration of the parent structure, and/or reliance on protective/prosthetic groups leading to lengthy multiple-step processes.

There is need for further radiolabeled amino acids suitable for PET imaging. Also there is a need for simple and robust synthesis processes for the preparation of radiolabeled amino acids and their derivatives, which can avoid precursor synthesis and the protective groups.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an $^{18}$F-labeled amino acids, derivatives thereof and method of making same. In accordance with an aspect of the present invention, there is provided a compound having a formula (I):

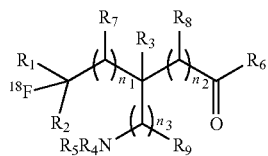

or a salt thereof or stereoisomers thereof, wherein:
n1, n2 and n3 are independently 0-5;
R1 is H or alkyl;
R2 is H or alkyl;
R3 is H, alkyl, cycloalkyl or aryl;
R4 is H, alkyl, COR10 or R11, wherein R10 and R11 are independently an amino acid residue or peptide;
R5 is H, alkyl, COR10 or R11, wherein R10 and R11 are independently an amino acid residue or peptide;
R6 is —OH, or NR12 R13, wherein R12 and R13 are independently H, alkyl, an amino acid residue, or a peptide residue; and
each occurrence of R7, R8 and R9 is independently H, alkyl, cycloalkyl or aryl.

In accordance with another aspect of the invention, there is provided a compound having formula:

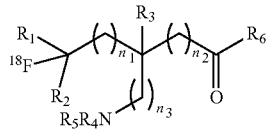

or a salt thereof or a stereoisomer thereof, wherein:
$n_1$, $n_2$ and $n_3$ are independently 0-5;
$R_1$ is H or C1-C6 alkyl;
$R_2$ is H or C1-C6 alkyl;
$R_3$ is H or C1-C6 alkyl,
$R_4$ is H, C1-C6 alkyl, or COR10 or R11, wherein R10 and R11 are independently an amino acid residue or peptide;
$R_5$ is H, C1-C6 alkyl, COR10 or R11, wherein R10 and R11 are independently an amino acid residue or peptide; and
$R_6$ is —OH, or $NR_{12}R_{13}$, wherein $R_{12}$ and $R_{13}$ are independently H, C1-C6 alkyl, or an amino acid residue or peptide.

The present disclosure provides novel $^{18}$F-labeled amino acids, which can be suitable for PET imaging.

The present disclosure also provides streamlined radiosynthetic process for preparation of $^{18}$F-labeled amino acids by direct fluorination of an un-activated tertiary or secondary C—H bond of an unprotected amino acid, without precursor synthesis and the protective groups.

In accordance with another aspect of the invention, there is provided a process of synthesizing a compound of formula (I) by reacting a compound of formula (I) reacting a compound of formula:

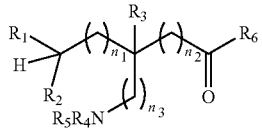

with [$^{18}$F]NFSI, in the presence of a decatungstate catalyst and a light source in an aqueous solvent.

In accordance with another aspect of the invention, there is provided methods and use of the compounds of formula (I) for PET imaging. In accordance with another aspect of the invention, there is provided methods and use of the compounds of formula (I) in diagnosis of proliferative diseases.

BRIEF DESCRIPTION OF THE FIGURES

FIG. 4: Radio TLC scan of [$^{18}$F]fluorination reaction of an exemplary embodiment in accordance with the present invention.
FIG. 5a: TLC analysis of a purified exemplary embodiment in accordance with the present invention (i.e., 4-[$^{18}$F]FL/leucine mixture) visualized with ninhydrin stain and radiodetection.
FIG. 5b: Radiodetected chiral HPLC analysis of an exemplary embodiment in accordance with the present invention (i.e. purified 4-[$^{18}$F]FL derived from L-leucine and DL-leucine.

DETAILED DESCRIPTION OF THE INVENTION

Definitions

Figure 1:
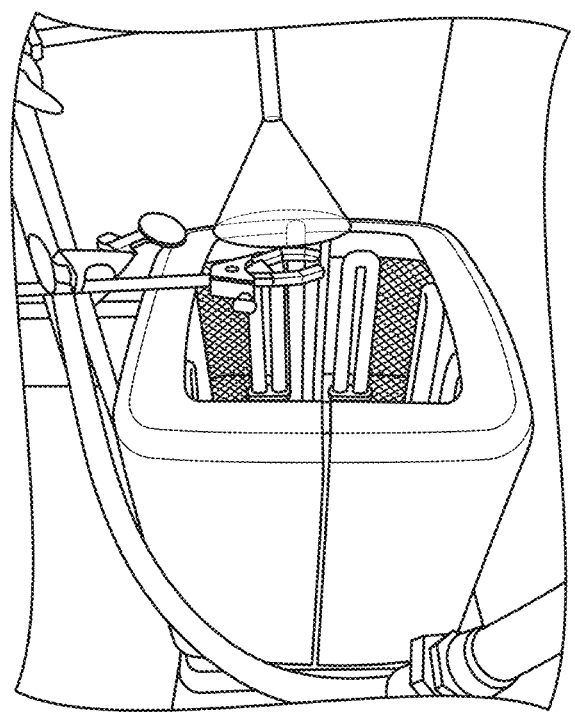
FIG. 1: A reactor configuration used in the process in accordance with an embodiment of the present invention.

Unless defined otherwise, all technical and scientific terms used herein have the same meaning as commonly understood by one of ordinary skill in the art to which this invention belongs.

The term "alkyl", as used herein refers to straight chain or branched chain, saturated or unsaturated alkyl group having 1 to 10 carbons, or 1 to 8 carbon atoms or 1 to 6 carbon atoms, preferably, straight chain or branched chain, saturated alkyl group having 1 to 10 carbons, or 1 to 8 carbon atoms or 1 to 6 carbon atoms.

The term "cycloalkyl", as used herein refers to saturated or unsaturated cyclic hydrocarbon group having 3 to 8 carbons, or 3 to 6 carbon atoms or 5 to 6 carbon atoms.

The term "aryl", as used herein refers to monocyclic or bicyclic aromatic hydrocarbon rings having 6 to 10 carbon atoms.

The term "amino acid residue", as used herein includes the portion of amino acid unit after reacting with NH$_2$ or COOH to form a peptide bond via removal of water molecule. Such groups are generally represented as —NH—R—COOH (which lacks a hydrogen atom of the amino group), or NH$_2$—R—CO— group (which lack hydroxyl moiety of the carboxyl group), or both (—NH—CHR—COO—).

The term "peptide", as used herein includes N-terminus or C-terminus, di-, tri-, tetra- and polypeptides, comprising two or more amino-acid residues. The residue in a peptide that has an free amino group that is free, is called N-terminal and the residue that has a free carboxyl group, is called C-terminal.

The terms "subject" or "patient," as used herein, refers to an animal in need of treatment, including humans and other mammals.

As used herein, the term "about" refers to approximately a +/−10% variation from a given value. It is to be understood that such a variation is always included in any given value provided herein, whether or not it is specifically referred to.

Radiolabeled Amino acids and Derivatives Thereof

The present invention provides novel $^{18}$F-labeled amino acids and derivatives thereof, having formula (I):

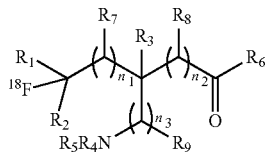

or a salt thereof or stereoisomers thereof, wherein:
n$_1$, n$_2$ and n$_3$ are independently 0-5;
R$_1$ is H or alkyl;

$R_2$ is H or alkyl;
$R_3$ is H, alkyl, cycloalkyl or aryl;
$R_4$ is H, alkyl, $COR_{10}$ or $R_{11}$, wherein $R_{10}$ and $R_{11}$ are independently an amino acid residue or peptide;
$R_5$ is H, alkyl, $COR_{10}$ or $R_{11}$, wherein $R_{10}$ and $R_{11}$ are independently an amino acid residue or peptide; and
$R_6$ is —OH, or $NR_{12}R_{13}$, wherein $R_{12}$ and $R_{13}$ are independently H, alkyl, an amino acid residue, or a peptide residue;
each occurrence of $R_7$, $R_8$ and $R_9$ is independently H, alkyl, cycloalkyl or aryl.

In some embodiments of compounds of formula (I):
$R_1$ is H or alkyl;
$R_2$ is H or alkyl;
$R_3$ is H, alkyl;
$R_4$ is H, alkyl, $COR_{10}$ or $R_{11}$, wherein $R_{10}$ and $R_{11}$ are independently an amino acid residue or peptide;
$R_5$ is H, alkyl, $COR_{10}$ or $R_{11}$, wherein $R_{10}$ and $R_{11}$ are independently an amino acid residue or peptide; and
$R_6$ is —OH, or $NR_{12}R_{13}$, wherein $R_{12}$ and $R_{13}$ are independently H, alkyl, an amino acid residue, or a peptide residue;
each occurrence of $R_7$, $R_8$ and $R_9$ is independently H or alkyl.

In some embodiments of compounds of formula (I):
$R_1$ is H or C1-C6 alkyl;
$R_2$ is H or C1-C6 alkyl;
$R_3$ is H or C1-C6 alkyl;
$R_4$ is H, C1-C6 alkyl, $COR_{10}$ or $R_{11}$, wherein $R_{10}$ and $R_{11}$ are independently an amino acid residue or peptide;
$R_5$ is H, C1-C6 alkyl, $COR_{10}$ or $R_{11}$, wherein $R_{10}$ and $R_{11}$ are independently an amino acid residue or peptide;
$R_6$ is —OH, or $R_{12}R_{13}$, wherein $R_{12}$ and $R_{13}$ are independently H, C1-C6 alkyl, or an amino acid residue or a peptide residue.

In some embodiments, the compounds of formula (I) comprise the compounds having formula (II):

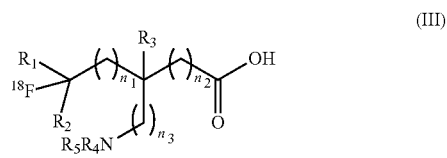

or a salt thereof or a stereoisomer thereof, wherein:
$n_1$, $n_2$ and $n_3$ are independently 0-5;
$R_1$ is H or alkyl;
$R_2$ is H or alkyl;
$R_3$ is H or alkyl;
$R_4$ is H, alkyl, $COR_{10}$ or $R_{11}$, wherein $R_{10}$ and $R_{11}$ are independently an amino acid residue or peptide;
$R_5$ is H, alkyl, $COR_{10}$ or $R_{11}$, wherein $R_{10}$ and $R_{11}$ are independently an amino acid residue or peptide; and
$R_6$ is —OH, or $NR_{12}R_{13}$, wherein $R_{12}$ and $R_{13}$ are independently H, alkyl, or an amino acid residue or a peptide residue.

In some embodiments of the compounds of formula (II):
$R_1$ is H or C1-C6 alkyl;
$R_2$ is H or C1-C6 alkyl;
$R_3$ is H or C1-C6 alkyl,
$R_4$ is H, C1-C6 alkyl, or $R_{11}$, wherein $R_{11}$ is an amino acid residue or peptide residue;
$R_5$ is H, C1-C6 alkyl, or $R_{11}$, wherein $R_{11}$ is an amino acid residue or peptide residue;
and
$R_6$ is —OH, or $NR_{12}HR_{13}$, wherein $R_{12}$ and $R_{13}$ are independently H, C1-C6 alkyl, or an amino acid residue or peptide.

In some embodiments of the compounds of formulae (I) and (II) described above, $n_1$, $n_2$ and $n_3$ are independently 0-4. In some embodiments of the compounds of formulae (I) and (II), $n_1$, $n_2$ and $n_3$ are independently 0-3.

In some embodiments, the compounds of formula (I) comprise the compounds having formula (III):

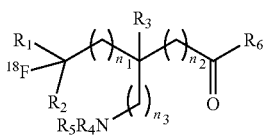

or a salt thereof, or a stereoisomer thereof, wherein:
$n_1$, $n_2$ and $n_3$ are independently 0-3;
$R_1$ is H or C1-C6 alkyl;
$R_2$ is H or C1-C6 alkyl;
$R_3$ is H or C1-C6 alkyl;
$R_4$ is H or C1-C6 alkyl, or R11, wherein R11 is an amino acid residue or peptide; and
$R_5$ is H, C1-C6 alkyl, or R11, wherein R11 is an amino acid residue or peptide.

In some embodiments of the compounds of formulae (I), (II) and (II) described above $R_3$ is H.

In some embodiments of the compounds of formulae (I), (II) and (III) described above, at least one of $R_1$ and $R_2$ is other than H. In some embodiments of the compounds of formulae (I) and (II), both of $R_1$ and $R_2$ are other than H.

In some embodiments of formulae (I), (II) and (III) described above, at least one of $R_1$ and $R_2$ is C1-C3 alkyl. In some embodiments, both of $R_1$ and $R_2$ are C1-C3 alkyl. In some embodiments, both of $R_1$ and $R_2$ are $CH_3$.

In some embodiments of formulae (I), (II) and (III) described above, one of $R_4$ and $R_5$ is H and the other one is $CH_3$. In some embodiments both of $R_4$ and $R_5$ are H.

In some embodiments of formulae (I), (II) and (III) described above, one of $R_4$ and $R_5$ is H or alkyl, and the other is $R_{11}$, wherein $R_{11}$ is a residue of a natural amino acid. In some embodiments, the amino acid residue is selected from lysine (K), aspargine (N), glycine (G), alanine (A), glutamic acid (E), phenylalanine (F), histidine (H) or aspartic acid (D).

In some embodiments, the amino residue is lysine or asparagine.

In some embodiments of formulae (I), (II) and (III) described above, one of $R_4$ and $R_5$ is H or alkyl, and the other is $R_{11}$, wherein $R_{11}$ is a peptide. In some embodiments, the peptide comprises natural amino acids. In some embodiments, the peptide is a di-, tri-, or tetra peptide of amino acids selected from lysine, aspargine, glycine, histidine, glutamic acid, aspartic acid, phenylalanine, glycine and alanine. In some embodiments, the peptide is a dipeptide of any two amino acids selected from lysine, aspargine, glycine, glutamic acid, phenylalanine, glycine and alanine.

In some embodiments of formulae (I), and (II) described above, $R_6$ is $NHR_{12}R_{13}$, wherein one of $R_{12}$ and $R_{13}$ is H or alkyl, and the other is a residue of a natural amino acid. In some embodiments, the amino acid residue is selected from lysine (K), aspargine (N), glycine (G), alanine (A), glutamic acid (E), phenylalanine (F), histidine (H) or aspartic acid (D).

In some embodiments, one of $R_{12}$ and $R_{13}$ is H or alkyl, and the other is a peptide. In some embodiments, the peptide comprises natural amino acids. In some embodiments, the peptide comprises natural amino acids. In some embodiments, the peptide is a di-, tri-, or tetra peptide of amino acids selected from lysine (K), aspargine (N), glycine (G), alanine (A), glutamic acid (E), phenylalanine (F), histidine (H) or aspartic acid (D). In some embodiments, the peptide is a dipeptide of any two amino acids selected from lysine (K), aspargine (N), glycine (G), alanine (A), glutamic acid (E), phenylalanine (F), histidine (H) or aspartic acid (D).

In some embodiments the peptide is a tripeptide GEA.

In some embodiments the peptide is a dipeptide selected from KA, AF, FE, AF or AE.

In some embodiments of formulae (I), (II) and (III) described above, alky is straight chain or branched chain, saturated alkyl group.

In some embodiments, —$NR_4R_5$ is $NH_2$.HA, and the compound is in the form of a salt, wherein A includes but not limited to trifluoroacetate ion (TFA), halide ion (X—), bisulfate ion ($HSO_4$—), mesylate ion (MSA-). In some embodiments, A is TFA, or halide ion. In some embodiments, X is chloride ion.

In some embodiments, the $^{18}$F-labeled amino acid is:

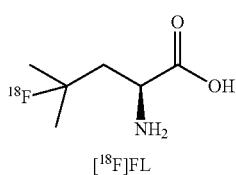

[$^{18}$F]FL (6)

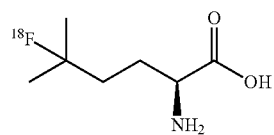

5-[$^{18}$F]FHL (7)

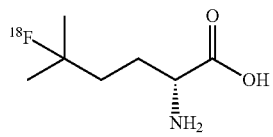

D-5-[$^{18}$F]FHL (8)

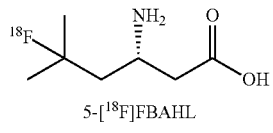

5-[$^{18}$F]FBAHL (9)

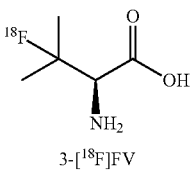

3-[$^{18}$F]FV (10)

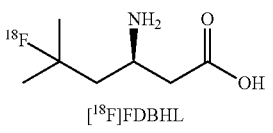

[$^{18}$F]FDBHL (11)

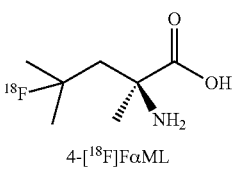

4-[$^{18}$F]FαML (12)

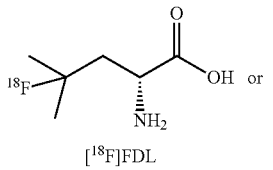

[$^{18}$F]FDL or (13)

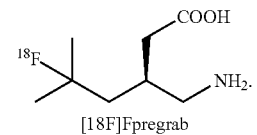

[18F]Fpregrab (14)

In some embodiments, the $^{18}$F-labeled compounds are selected from:

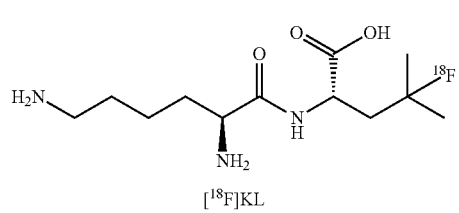

[$^{18}$F]KL (15)

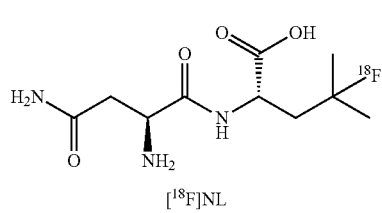

[$^{18}$F]NL (16)

-continued

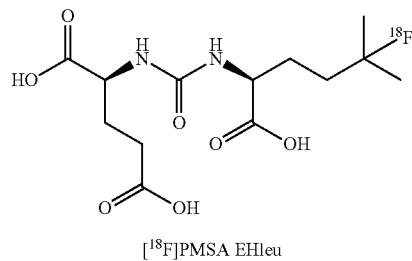

[18F]PMSA EHleu (17)

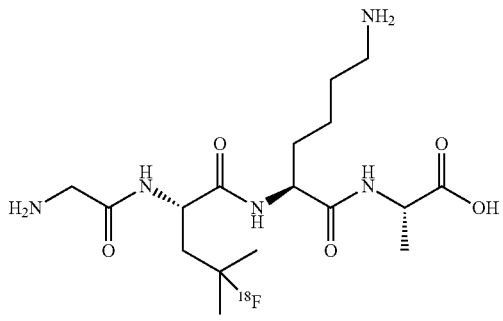

[18F]GLKA (18)

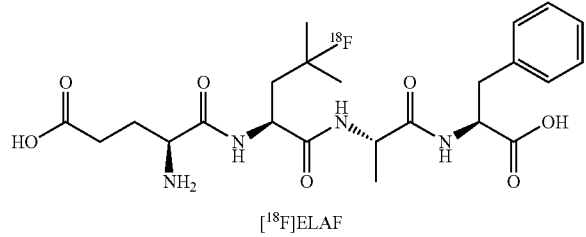

[18F]ELAF (19)

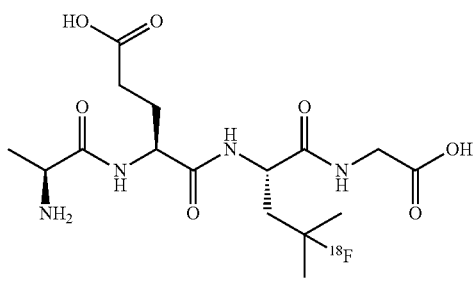

[18F]AELG (20)

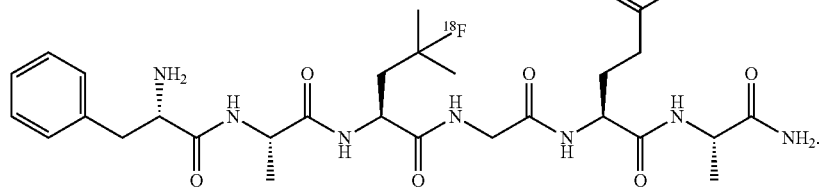

[18F]FALGEA (21)

In some embodiments, the $^{18}$F-labeled compounds are selected from:

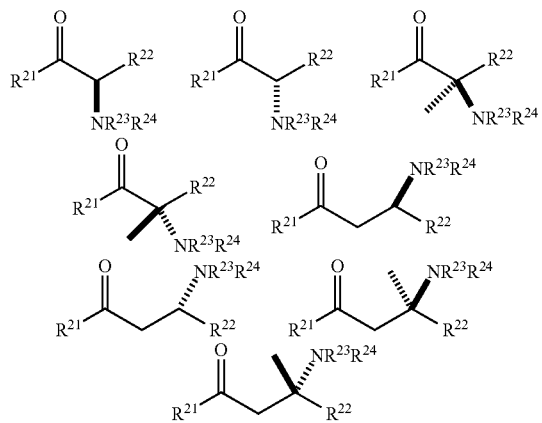

or any acceptable salt derived from these compounds $R^{21}$=OH, NH$_2$, or NHR$^{26}$ $R^{23}$=H, alkyl (branched or linear), amino acid residue or peptide, COR$^{27}$ $R^{24}$=H, alkyl (branched or linear), amino acid residue or peptide, COR$^{27}$ $R^{26}$=amino acid residue or peptide $R^{27}$=amino acid residue or peptide $R^{22}$ =

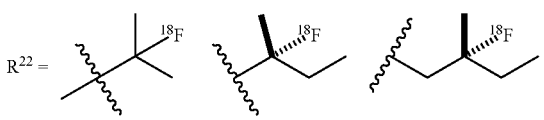
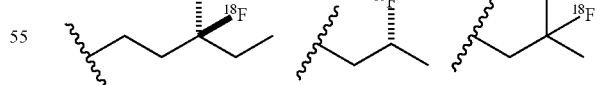
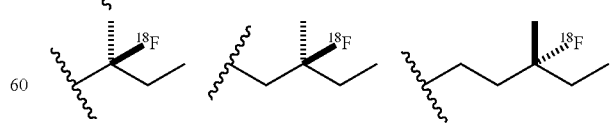

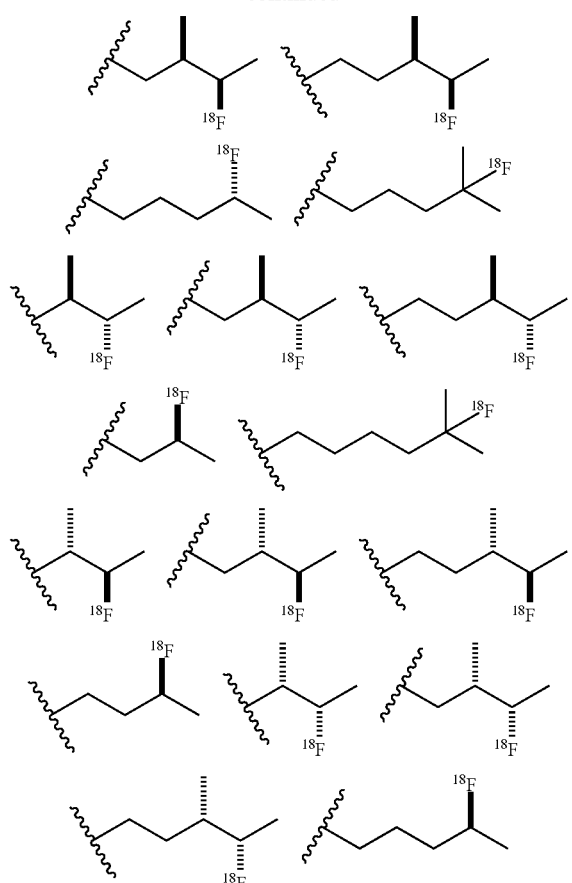

In some embodiments, the $^{18}$F-labeled compounds are selected from:

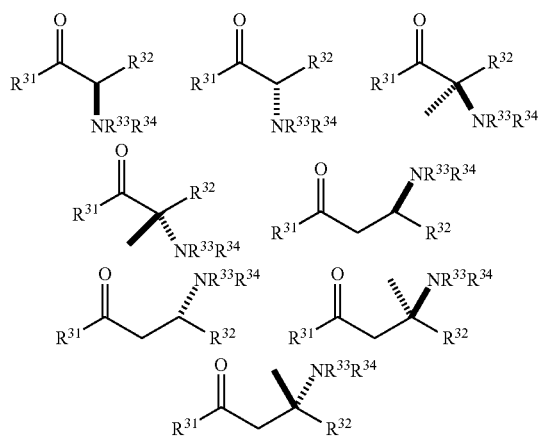

or any acceptable salt derived from these compounds $R^{31}$=OH, NH$_2$, or NHR$^{36}$ $R^{33}$=H, alkyl (branched or linear)

$R^{36}$=alkyl (branched or linear) or amino acid residue or peptide

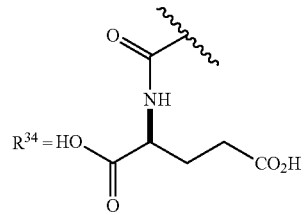 [SMILES: *C(=O)N[C@@H](CCC(=O)O)C(=O)O]

$R^{32}$ = 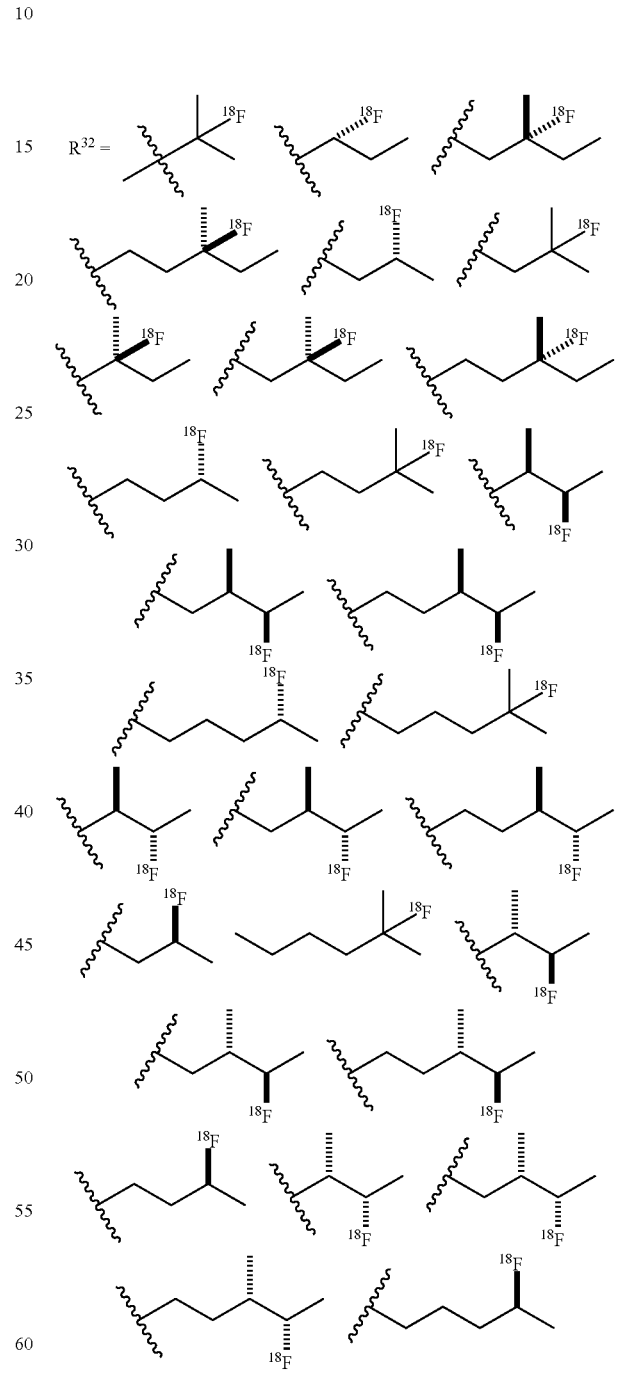

Use of Radiolabeled Compounds

Radiolabeled compounds of the present invention can be used in the manufacture of an imaging tracer or radiopharmaceutical agent for imaging proliferative diseases. The imaging agent or radiopharmaceutical agent is preferably suitable as imaging agent for PET applications.

In some embodiments, the radiolabeled compounds of the present invention can be used as imaging tracers or radiopharmaceutical agents. In some embodiments, the radiolabeled compounds of the present invention can be used for PET imaging.

The present invention is also directed to a method of PET imaging comprising the step of introducing into a subject a detectable quantity of an $^{18}F$ labeled compounds of the present invention and obtaining a PET image of said subject.

The invention is also directed to a method of diagnosing diseases comprising the steps:
administering to a subject an effective amount of a radiolabeled compound of the present invention;
obtaining images of the subject; and assessing the images.

In preferred embodiments the use/method is directed to the diagnosis of proliferative diseases.

Another aspect of the invention is the use of $^{18}F$ labeled compounds of the present invention as described above for diagnosing and/or treating oncology disease in a patient, in particular in a mammal, such as a human.

Proliferative diseases in oncology are characterized by the presence of tumor and/or metastases. Preferably tumors include but are not limited to malignomas of the gastrointestinal or colorectal tract, liver carcinoma, pancreas carcinoma, kidney carcinoma, bladder carcinoma, thyroid carcinoma, prostate carcinoma, endometrial carcinoma, ovary carcinoma, testes carcinoma, melanoma small-cell and non-small-cell lung carcinoma, dysplastic oral mucosa carcinoma, invasive oral cancer; breast cancer, including hormone-dependent and hormone-independent breast cancer, squamous cell carcinoma, neurological cancer disorders including neuroblastoma, glioma, astrocytoma, osteosarcoma, meningioma, soft tissue sarcoma, haemangioma and endocrine tumors, including pituitary adenoma, chromocytoma, paraganglioma, haematological tumor disorders including lymphoma and leukaemias.

In some embodiments, the radiolabeled amino acids of the present invention are useful in PET imaging of glioma, prostate cancer and/or tumours.

Another aspect of the invention is directed to a method of imaging cancers/tumors. Such a method comprises a) administering to a mammal a radiolabeled compounds as described above containing a detectable label, and b) detecting the signals, for example, stemming from increased amino acid uptake in cancer cells/tumor, or the binding of a peptide/amino acid to a receptor within the cell or on the cell surface, or from the metabolic incorporation of a peptide/amino acid in the dysregulated metabolism present in cancer cells.

In some embodiments, methods of diagnosing and use for PET imaging of proliferative diseases involve administration of one or more compounds of formula (III) as described above.

In some embodiments, methods of diagnosing and use for PET imaging of proliferative diseases involve administration of one or more compounds listed below:

6

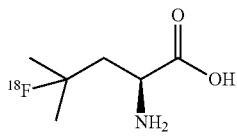

-continued

7

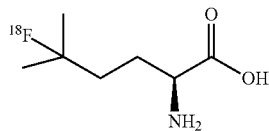

8

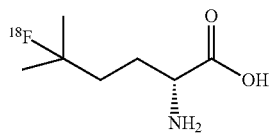

9

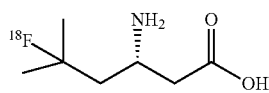

10

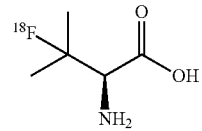

11

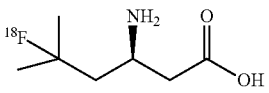

12

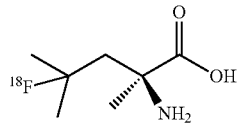

13

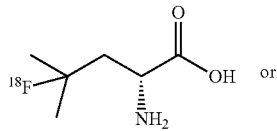 or

14

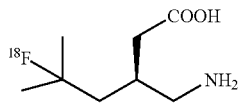

In some embodiments, methods of diagnosing and PET imaging of proliferative diseases involve administration of compound is 5-[$^{18}F$]fluorohomoleucine (5-[$^{18}F$]FHL).

In some embodiments, methods of diagnosing and use for PET imaging of proliferative diseases involve administration of one or more compounds listed below.

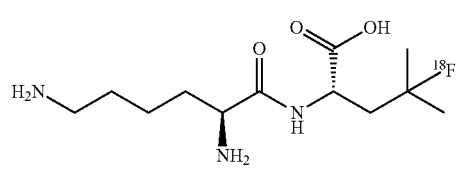
(15)

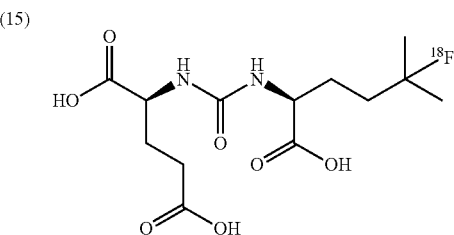
(16)

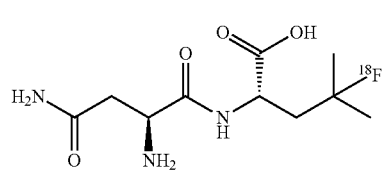
(17)

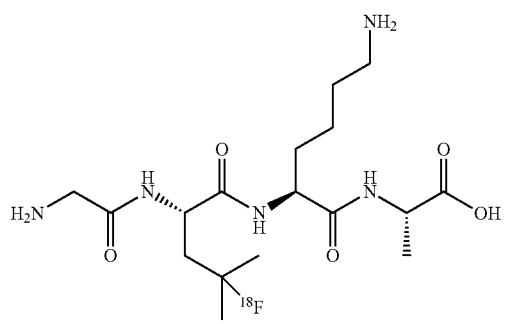
(18)

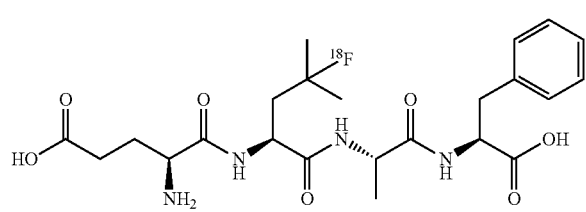
(20)

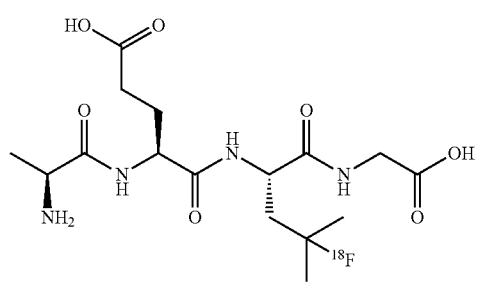
(19)

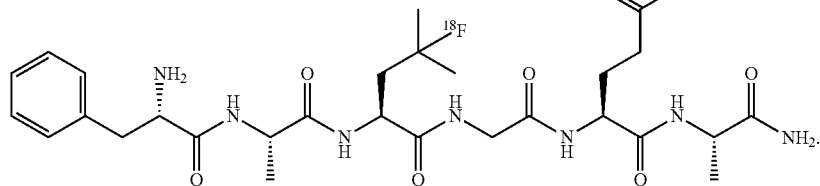
(21)

In Vitro Testing

Candidate radiolabeled amino acid compounds can be tested/assayed initially in vitro for their ability to act as a radio tracer or PET imaging agent using standard techniques known in the art, for example, by conducting cell uptake studies with appropriate cell lines.

A wide variety of cancer cell lines suitable for testing the radiolabeled compounds of Formulae (I), (II) and (III) are available commercially, for example the American Type Culture Collection (ATCC) and the DCTD Tumor Depository (NCI) supplies a variety of mammalian cell lines, including the human cancer cell lines used in the NCI/NIH screen.

Examples of suitable human cancer cell-lines against which the compounds of the present invention can be tested include, but are not limited to, prostate adenocarcinoma and carcinoma cell lines LNCaP, PC-3, MDA PCa 2b, LNCaP-FGC and 22Rv1, breast cancer cell lines such as MCF-7, MDA-MB-435, NCI/ADR-RES MDA-N, MDA-MB-231/ATCC, BT-549, HS 578T, brain cancer/tumour cell lines, such as U87-MG, U118-MG, bladder cancer cell lines HT-1376, HT-1197, and Hs 195.T; colon and colorectal adenocarcinoma and carcinoma cell lines such as CaCo, COLO320, HCT-116, LoVo, NCI-H498, NCI-H548 and SNU-C2B; duodenal cancer cell line HuTu 80; gastric adenocarcinoma and carcinoma cell lines Hs 740.T, AGS, Hs 746T, NCI-N87, NCI-SNU-1 and RF-48; large cell lung cancer cell lines NCI-H661 and NCI-H1581; Burkitts lymphoma (Non-Hodgkin's) cell lines raji, Namalwa and HS Sultan; histiocytic lymphoma cell line U-937; acute lymphoblastic leukemia (T-ALL) cell line Jurkat, T-cell lymphoma cell line Karpas 299; plasma cell leukemia cell line L-363; and rectal adenocarcinoma and carcinoma cell lines NCI-H630 and SW837.

In Vivo Testing

The ability of the candidate radiolabeled amino acid compounds to as a radio tracer or PET imaging agent in vivo can be determined in an appropriate animal model using standard techniques known in the art, for example, via biodistribution studies and xenograft imaging.

Xenograft models, in which a human cancer or tumour has been implanted into an animal, is a standard model for assessing uptake of a candidate compound. Examples of xenograft models of human cancer include, but are not limited to, human solid tumour xenografts, implanted by sub-cutaneous injection or implantation and used in tumour growth assays; human solid tumour isografts, implanted by fat pad injection and used in tumour growth assays; human solid tumour orthotopic xenografts, implanted directly into the relevant tissue and used in tumour growth assays; disseminated disease models for solid tumours or for leukemias, via intravenous injection, used in survival assays; experimental models of lymphoma and leukaemia in mice, used in survival assays, and experimental models of lung metastasis in mice. In addition to the implanted human tumour cells, the xenograft models can further comprise transplanted human peripheral blood leukocytes, which allow for evaluation of the anti-cancer immune response. In various xenograft models, the implanted or transplanted human tumour cells can be primary tumour cells or tumour cells derived from a cell line.

Several host animal options exist for xenograft models, which includes but are not limited to the use of severe combined immunodeficient (SCID) mice, athymic nude mice, and athymic rats. Non-obese diabetic/severe combined immunodeficient mice (NOD/SCID) represent another host animal that can be used in various xenograft transplantation models, for example, for the engraftment of hematological cancer cells, such as leukemia and/or lymphoma cells.

Process of Synthesising $^{18}$F labeled Amino Acids and Derivatives Thereof

In accordance with another aspect of the present invention, there is provided a process for the preparation of $^{18}$F-labeled amino acids or derivative thereof by direct fluorination of an un-activated C—H bond in the starting compound.

In some embodiments, the process comprises reacting a compound of formula (IV):

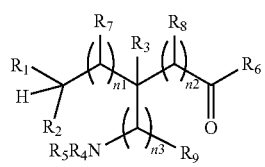

(IV)

wherein $R_1$ to $R_9$ are as defined above, with a suitable $^{18}$F-fluorinating agent, in the presence of a suitable catalyst and a light source in an aqueous solvent to form a compound of formula (I).

In some embodiments the process comprises reacting the compound of formula (VI) with [$^{18}$F]N-Fluorodibenzenesulfonimide ([$^{18}$F]NFSI), in the presence of a decatungstate catalyst and a light source in a aqueous solvent.

In some embodiments, the process comprises reacting a compound of formula (V):

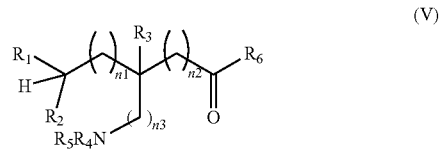

(V)

wherein $R_1$ to $R_6$ are as defined above, with a suitable $^{18}$F-fluorinating agent, in the presence of a suitable catalyst and a light source in an aqueous solvent to form a compound of formula (II).

In some embodiments the process comprises, reacting the compound of formula (VI) with [$^{18}$F]NFSI, in the presence of a decatungstate catalyst and a light source in a aqueous solvent.

In accordance with another aspect of the present invention, there is provided a process for the preparation of $^{18}$F-labeled amino acids by direct fluorination of an un-activated C—H group in an un-protected amino acid having formula (VI):

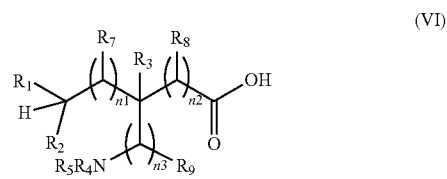

(VI)

The process comprises, reacting the compound of formula (VI) with a suitable $^{18}$F-fluorinating agent, in the presence of a suitable catalyst and a light source in an aqueous solvent to form a compound of formula (III).

In some embodiments the process comprises reacting the compound of formula (VI) with [$^{18}$F]NFSI, in the presence of a decatungstate catalyst and a light source in a aqueous solvent.

In some embodiments, the decatungstate catalyst is ammonium paratungstate (APT), tributylammonium decatungstate (TBADT) or sodium decatungstate (NaDT).

In some embodiments, the decatungstate catalyst is sodium decatungstate (NaDT).

In some embodiments, the radio labeling fluorination reaction involves reacting the compound of formula (IV), (V) or (VI) with 1-10 molar equivalents of the fluorinating agent.

In some embodiments, the aqueous solvent is water, a water miscible soluble organic solvent or a solvent mixture comprising a water miscible organic solvent and water. Examples of water miscible organic solvents include, but are not limited to $CH_3CN$, acetone, benzene, DMSO or mixtures thereof.

In some embodiments, the water miscible organic solvent is $CH_3CN$.

In some embodiments, the fluorination reaction is carried out in a solvent mixture comprising $CH_3CN$ and $H_2O$ in a ratio from about 10: to 1:1. In some embodiments, the ratio of $CH_3CN$ and $H_2O$ is about 9:1 to 2:1. In some embodiments, the ratio of $CH_3CN$ and $H_2O$ is about 6:1 to 3:1.

In some embodiments, the light source is a mercury lamp, a xenon lamp, a deuterium lamp, a tungsten halogen lamp (also known as a quartz iodine lamp), a light-emitting diode (LED), a UV-Vis lamp emitting light in the wavelength range 200-500 nm, or sunlight.

In some embodiments, the light source is a 365 nm UV lamp.

In some embodiments, the fluorination reaction is carried out in a reactor having 8×9W UV curing lamps in a "box" configuration with air cooling (FIG. 1). Such a reactor can comprise 8×9W UV curing lamps in "box" configuration with air cooling.

Figure 2:
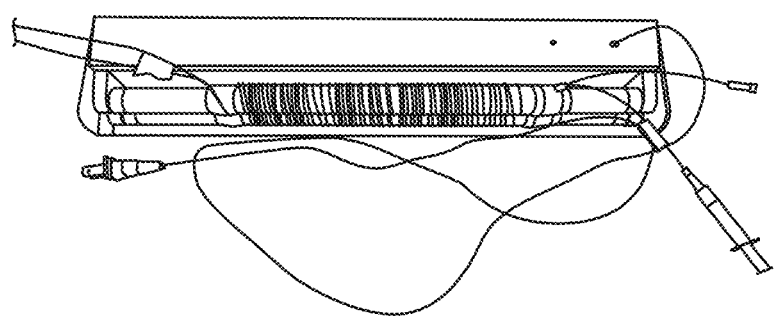
FIG. 2: A reactor configuration used in the process in accordance with an embodiment of the present invention.

In some embodiments, the fluorination reaction is carried out in a PTFE tube wrapped around a UV lamp (such as BLB lamp) (FIG. 2). Such a reactor configuration can comprise 15 W F15T8/BLB lamp and PTFE reaction tube (Hamilton, 3 m length, 0.7 mm inner diameter (ID), 1.9 mm outer diameter (OD), ~2.5 mL total volume).

Figure 3:
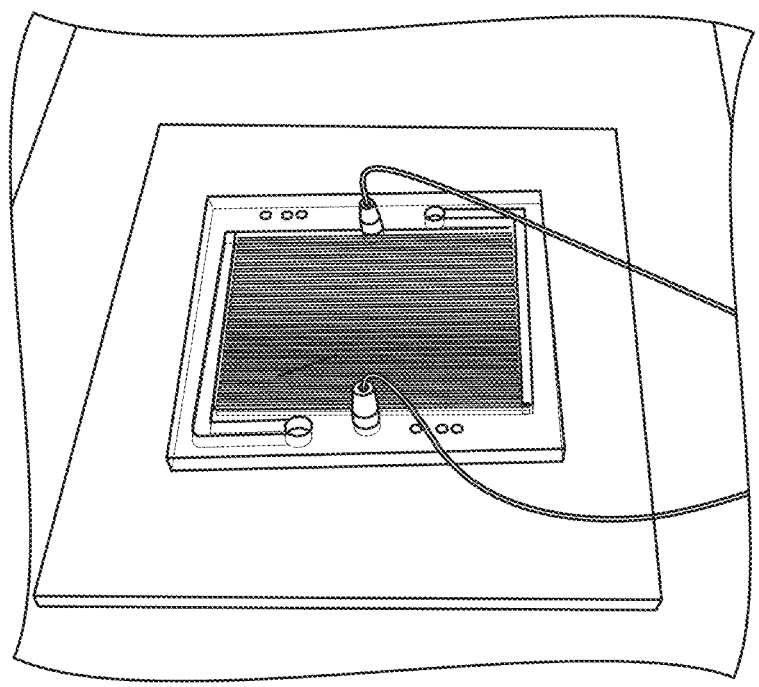
FIG. 3: A reactor configuration used in the process in accordance with an embodiment of the present invention.
Figure 6:
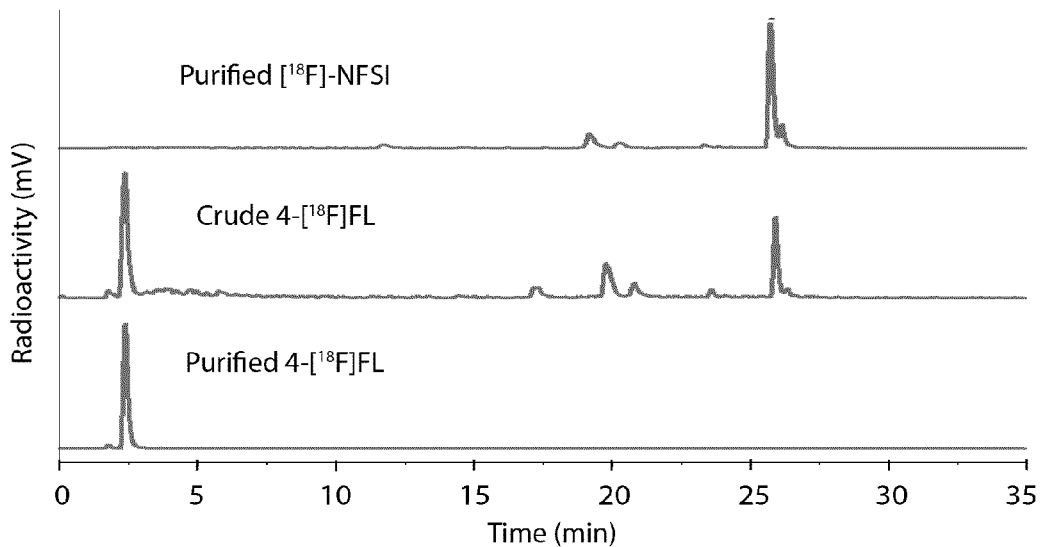
FIG. 6: Radiodetected HPLC traces for radiosynthesis of an exemplary embodiment in accordance with the present invention (i.e. 4-[$^{18}$F]FL).

In some embodiments, the fluorination reaction is carried out in a reactor having a "chip" configuration (FIG. 3). Such a reactor comprises, for example, a borosilicate glass microreactor placed on a 100 W (4×25 W bulbs) UV transilluminator (Jena Analytik) set to 365 nm.

Other reactor configurations of narrow-bore PTFE or glass tubing, glass microreactors, thin film slides, open bath containers can also be used in the process of the present invention.

In some embodiments, $[^{18}F]$NFSI used in the fluorination process of the present invention can be prepared via methods known in the art, for example in Gouverneur, et al. *Chem. Commun.* 2007, 2330, incorporated herein by reference.

In some embodiments, $[^{18}F]$NFSI used in the fluorination process of the present invention is prepared via a 5-10 min cyclotron irradiation of $[^{18}O]O_2$ produced $[^{18}F]F_2$ gas from which ~1.5 GBq is trapped in the $NaN(SO_2Ph)_2 \rightarrow [^{18}F]$NFSI reaction mixture.

In some embodiments, the $[^{18}F]$NFSI is purified via solid phase extraction using silica based stationary phase, in the absence of drying of $[^{18}F]$NFSI by azeotropic distillation as generally required for use of this reagent. In some embodiments, the silica based stationary phase is C18 SepPak cartridge.

In some embodiments, the process further includes passing the reaction mixture after fluorination step through a cation exchange resin to remove by-products and unreacted NFSI from the amino acids.

Contrary to the well-established understanding in the field of synthetic organic chemistry, the inventors of the present invention have established that $^{18}F$-labeled amino acid can be prepared by direct fluorination of unprotected amino acids, without any precursor synthesis and without use of protecting/prosthetic groups.

The process of the present invention can be carried out at room temperature in aqueous solution, thereby not requiring drying of reagents or solvent switches. Therefore the reaction products require minimal purification and material manipulation, and the products can be isolated as suitable formulation for intravenous (IV) injection.

Moreover, the process of the present invention requires a short radiosynthesis time, and does not result in racemization of starting material or products, and therefore provides substantially enantio-pure products.

The mild and robust $^{18}F$-labeling process of the present invention can provide ready/easy access to radiolabeled amino acids for rapid proof-of-feasibility and/or activity studies on a variety of related amino acids and biomolecules, and enable the high throughput production and screening of radiotracers.

In addition, the radiolabeling process of the present invention also provides for the direct $^{18}F$-fluorination of native peptides.

To gain a better understanding of the invention described herein, the following examples are set forth. It will be understood that these examples are intended to describe illustrative embodiments of the invention and are not intended to limit the scope of the invention in any way.

EXAMPLES

A) Preparation of Compounds

Example 1: Production of $[^{18}F]F_2$ Gas $[^{18}F]F_2$ gas was produced on $TR_{13}$ cyclotron via the $^{18}O(p,n)^{18}F$ nuclear reaction in an aluminium-body target using two proton irradiations. First $[^{18}O]O_2$ was loaded into the target to ~270 psi and irradiated with 25 µA of 13 MeV protons for 5-10 minutes. The gas was removed under reduced pressure and cryogenically trapped for recycling. $F_2$ gas (3% in Ar) was filled into the target to 14 psi and topped with Ar to 290 psi. The target was then irradiated for 2-5 min with 20 µA of 13 MeV protons.

Example 2: Synthesis of $[^{18}F]$V-fluorodibenzene-sulfonamide ($[^{18}F]$NFSI)

Sodium dibenzenesulfonamide (20 mg, 62 µmol) was dissolved in 800 µL of 3:1 $CH_3CN:H_2O$ and placed in a conical vial. $[^{18}F]F_2$ produced in the cyclotron target was then passed through the solution over a period of ~15 min. The waste gas was trapped by saturated KI solution. Typically 1-2 GBq was trapped in the reaction mixture. The resulting solution was then passed through a SepPak (Waters tC18 SepPak Plus Long Cartridge). The cartridge was washed with 10 mL $H_2O$ followed by 600 µL $CH_3CN$. $[^{18}F]$NFSI was then eluted from the SepPak cartridge in 1.2 mL $CH_3CN$. Typically, 21±8 µmol of purified NFSI with an activity of 0.2-0.5 GBq is produced from this process. The amount of NFSI generated in each reaction was calculated following HPLC analysis of the reaction mixture and comparison with a calibration curve prepared from NFSI.

Example 3: Synthesis of (4-$[^{18}F]$FL, Compound 6)

About 20 µmol of $[^{18}F]$NFSI in a 6:1 mixture of MeCN—$H_2O$, was added to a slurry of L-leucineHCl=10 mg (55 µmol), and sodium decatungstate (NaDT, 5 mg, 2.0 µmol in 200-400 µL $H_2O$ and mixed briefly. The solution was then loaded onto a photoreactor as shown in FIG. 2, and irradiated for 40 min. After this time the solution was removed and the PTFE tube was washed with $CH_3CN$ (5 mL). The resulting solution was loaded onto a preconditioned strong cation exchange cartridge (Silicycle, 500 mg resin) and the cartridge was washed with $CH_3CN$ (10 mL) followed by $H_2O$ (10 mL). $^{18}F$-label compound was then eluted from the cartridge with 1 mL aliquots of 150 mM $NaHCO_3$, yielding a mixture of fluorinated amino acid and unreacted amino acid. The bulk of the activity was typically eluted in the $4^{th}$ and $5^{th}$ 1 mL aliquot. Analytical HPLC was carried out on Phenomenex Monolithic C18 analytical column (4.6×100 mm column, 1 mL/min) using a gradient of 2% solvent A (0.1% TFA in $H_2O$) and 98% solvent B (0.1% TFA in $CH_3CN$) to 100% solvent B over 30 min or on a Phenomenex Luna C18 (4.6×100 mm, 1 mL/min) using a gradient of 100% solvent A (0.1% TFA in H$_2$O) to 100% solvent B (0.1% TFA in CH$_3$CN) over 15 min.

RadioTLC analysis was carried out in BuOH:H$_2$O:HOAc (12:5:3), followed by ninhydrin staining and radioTLC detection.

4-[$^{18}$F]FL (compound 6) produced using this method has a specific activity of 7.1 MBq/μmol (±1.9 MBq/μmol, n=4), radiochemical purity of >97%, radiochemical yield of 23.3% (±3.3%) in a total radiosynthesis reaction time of 60 min.

To determine the enantiopurity of $^{18}$F-labeled compounds, the above reaction was carried out simultaneously with both racemic and enantiomerically pure form (i.e. DL-leucine and L-leucine for the above case) and the final products were analyzed by Chiral HPLC eluting on a Phenomenex D-Penicillamine 4.6×100 mm column, 1 mL/min, isocratic, 20% EtOH and 80% 1 mM aq. CuSO$_4$.

FIG. 4 illustrates radioTLC scan of crude leucine[18F] fluorination reaction.

FIG. 5a illustrates TLC analysis of purified 4-[$^{18}$F]FL/leucine mixture visualized with ninhydrin stain and radiodetection. FIG. 5b illustrates radiodetected chiral HPLC analysis of purified 4-[$^{18}$F]FL derived from L-leucine and DL-leucine.

FIG. 5 illustrates radiodetected HPLC traces for radiosynthesis of 4-[$^{18}$F]FL (compound 6).

Figure 7:
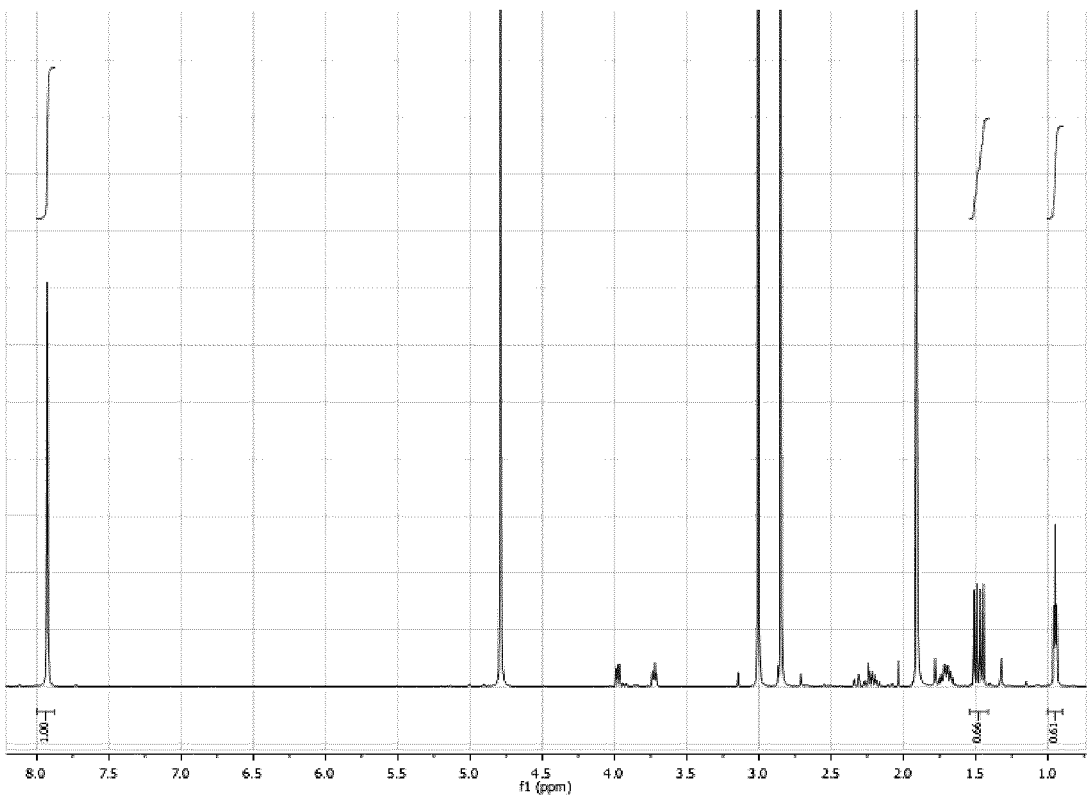
FIG. 7: $^1$H NMR spectrum (500 MHz, $D_2O$) of purified 4-[$^{18}$F]FL/leucine mixture after ~100 h decay at –20° C.

FIG. 7 illustrates $^1$H NMR spectrum (500 MHz, D$_2$O) of purified 4-[$^{18}$F]FL/leucine mixture after ~100 h decay at −20° C.

Figure 8:
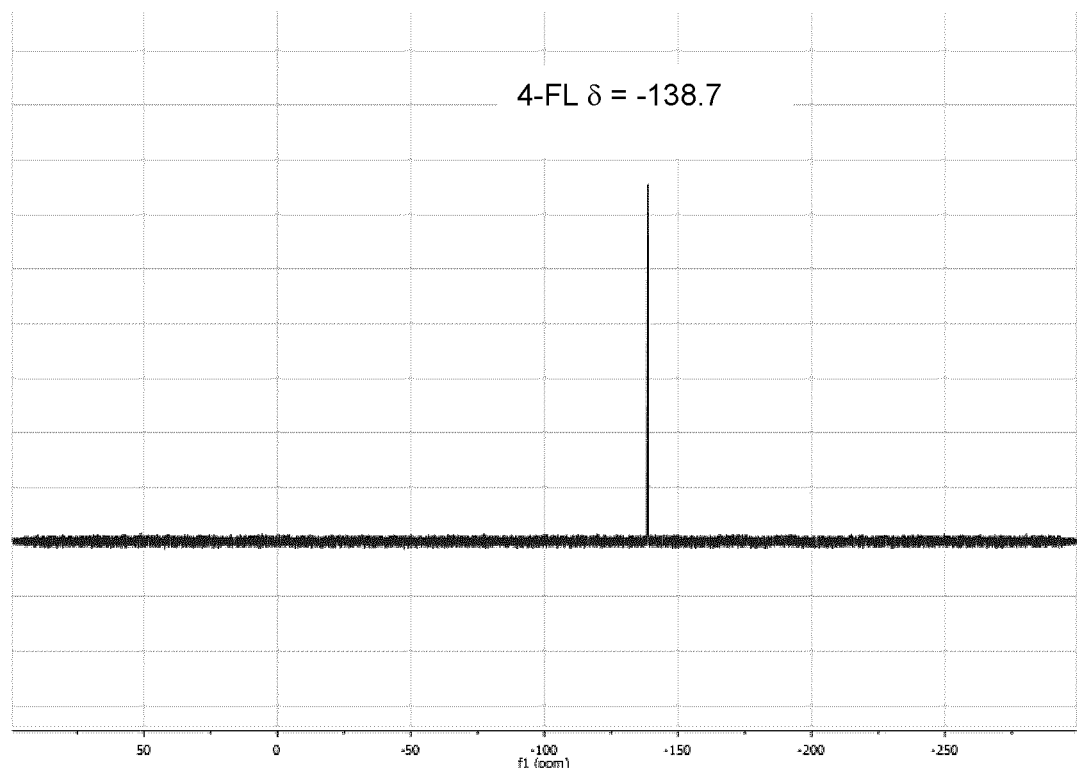
FIG. 8: $^{19}$F NMR spectrum (470 MHz, $D_2O$) of purified 4-[$^{18}$F]FL/leucine mixture after ~100 h decay at –20° C.

FIG. 8 illustrates $^{19}$F NMR spectrum (470 MHz, D$_2$O) of purified 4-[$^{18}$F]FL/leucine mixture after ~100 h decay at −20° C.

Examples 4 to 6: Synthesis of (5-[$^{18}$F]FHL, Compound 7), (5-[$^{18}$F]BAHL, Compound 9) and (3-[$^{18}$F]FV, Compound 10)

5-[$^{18}$F]FHL, 5-[$^{18}$F]FBAHL and 3-[$^{18}$F]FV were also prepared following the procedure as discussed above with respect to 4-[$^{18}$F]FL in example 3.

In particular, the [$^{18}$F]NFSI solution was added to a slurry of the substrate (β-aminohomoleucineTFA=13 mg (50 μmol), or homoleucineTFA=12 mg (46 μmol) or valineTFA=12 mg (52 μmol) and sodium decatungstate (NaDT, 5 mg, 2.0 μmol) in 200-400 μL H$_2$O and mixed briefly, followed by the procedure as described in example 3.

5-[$^{18}$F]FHL (compound 7) produced using this method has a specific activity of 6.3 MBq/μmol (±0.9 MBq/μmol, n=3), radiochemical purity of >97%, radiochemical yield of 27.9% (±3.3%), with radiosynthesis reaction time of ~60 min.

5-[$^{18}$F]FBAHL (compound 9) produced using this method had a specific activity of 2.2 MBq/μmol, a radiochemical purity >97%, the radiochemical yield of (29.8% (±0.7%)), with total radiosynthesis reaction time (~60 min).

3-[$^{18}$F]FV (compound 10) produced using this method had a specific activity of 3.4 MBq/μmol, a radiochemical purity >97% the radiochemical yield of 6.4%, with radiosynthesis reaction time (~60 min).

Figure 9:
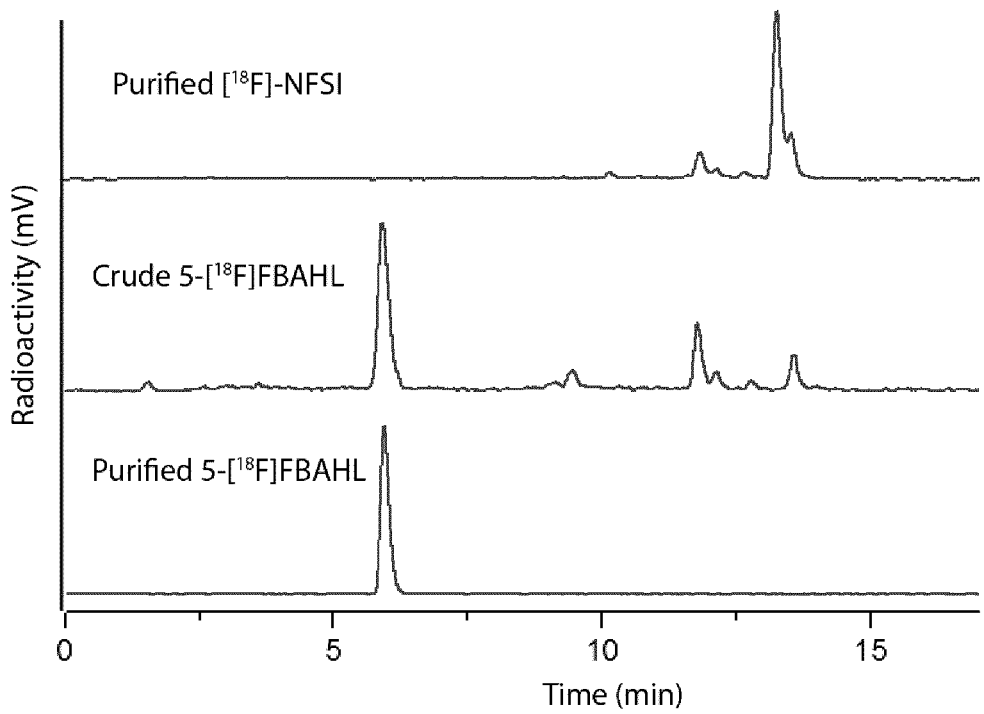
FIG. 9: Radiodetected HPLC traces for radiosynthesis of an exemplary embodiment in accordance with the present invention (i.e. 5-[$^{18}$F]FBAHL).
Figure 10:
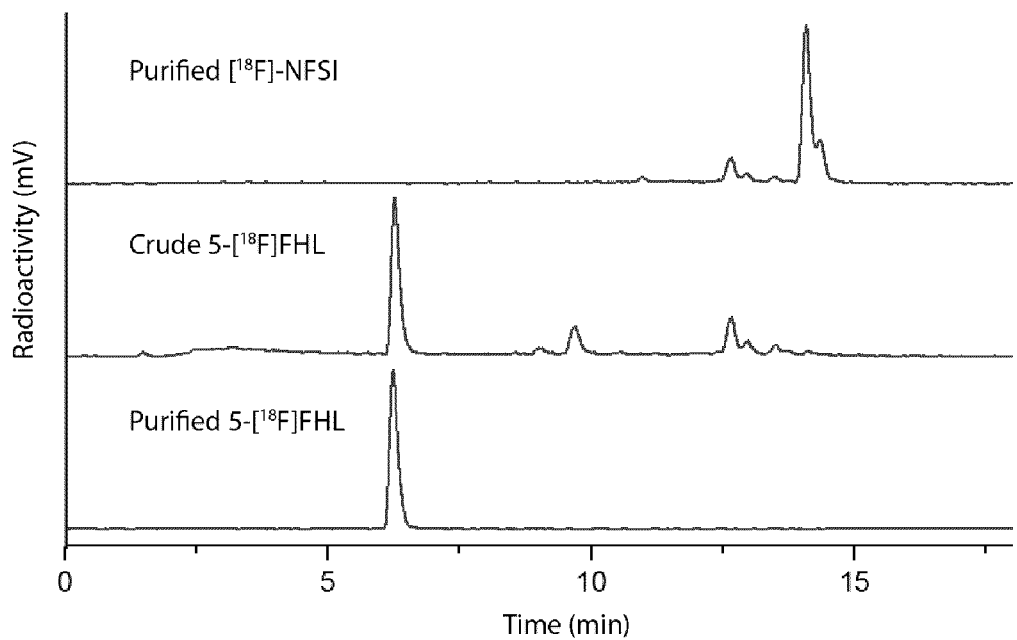
FIG. 10: Radiodetected HPLC traces for radiosynthesis of an exemplary embodiment in accordance with the present invention (i.e. 5-[$^{18}$F]FHL).
Figure 11:
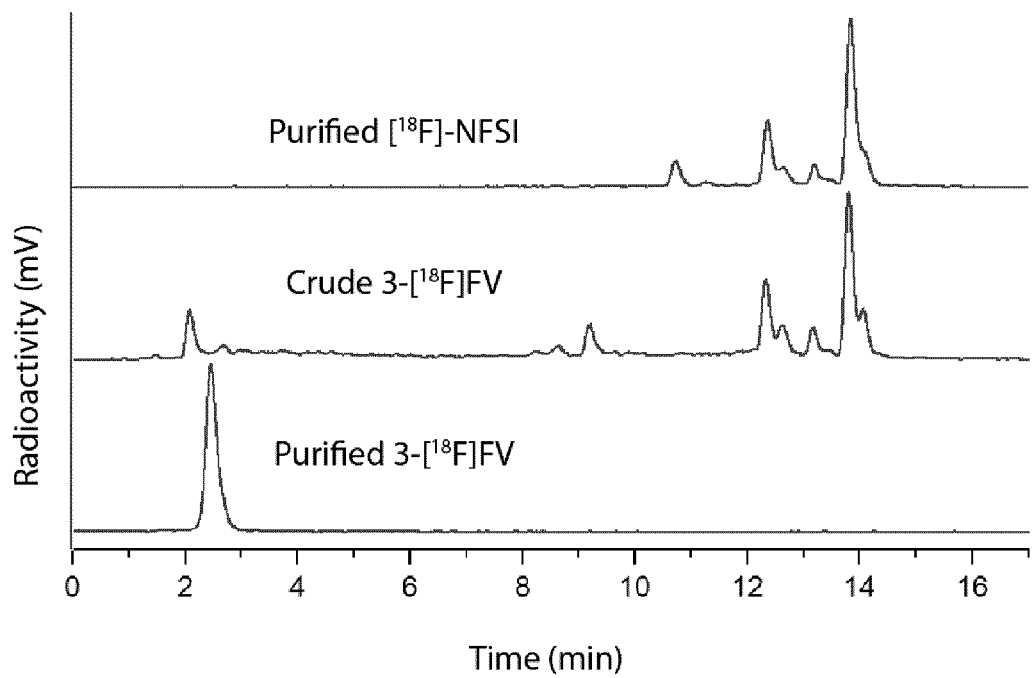
FIG. 11: Radiodetected HPLC traces for radiosynthesis of an exemplary embodiment in accordance with the present invention (i.e. 3-[18F]FV).

FIGS. 9 to 11 illustrate radiodetected HPLC traces for radiosynthesis of 5-[$^{18}$F]FBAHL, 5-[$^{18}$F]FHL, 3-[$^{18}$F]FV, respectively.

Figure 12:
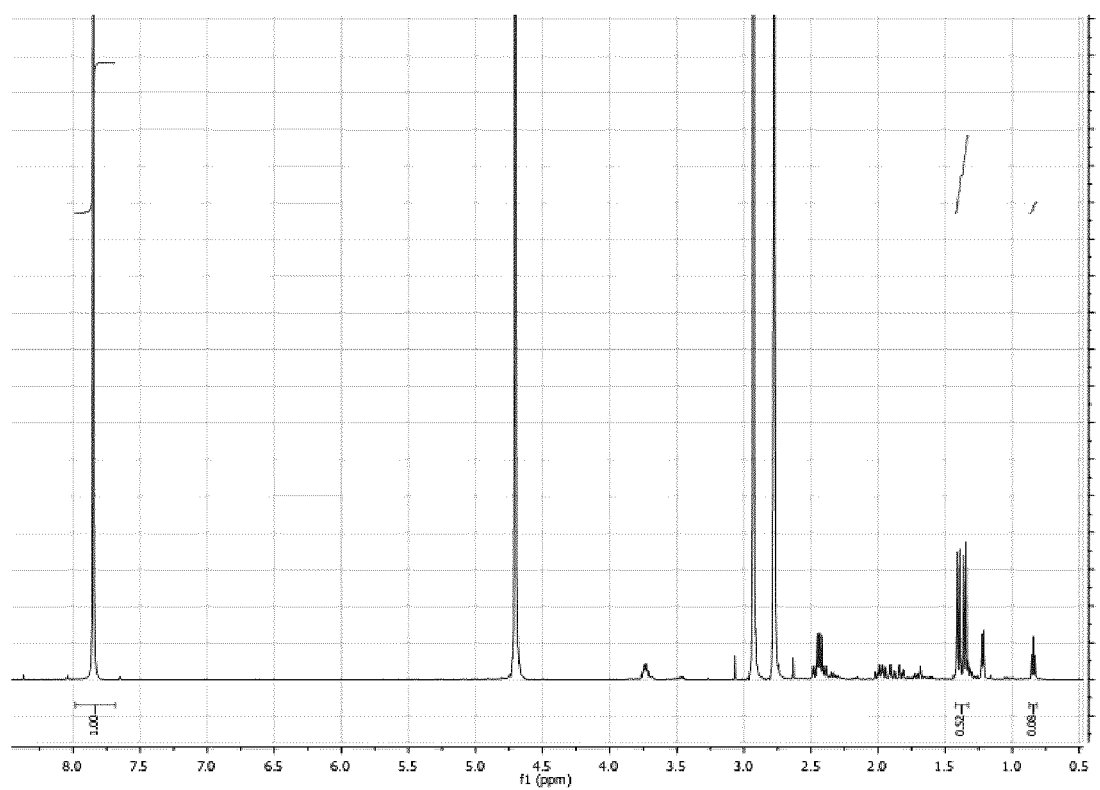
FIG. 12: $^1$H NMR spectrum (500 MHz, $D_2O$) of purified 5-[$^{18}$F]FBAHL/β-homoleucine mixture after ~100 h decay at –20° C.

FIG. 12 illustrates the $^1$H NMR spectrum (500 MHz, D$_2$O) of purified 5-[$^{18}$F]FBAHL/β-homoleucine mixture after ~100 h decay at −20° C.

Figure 13:
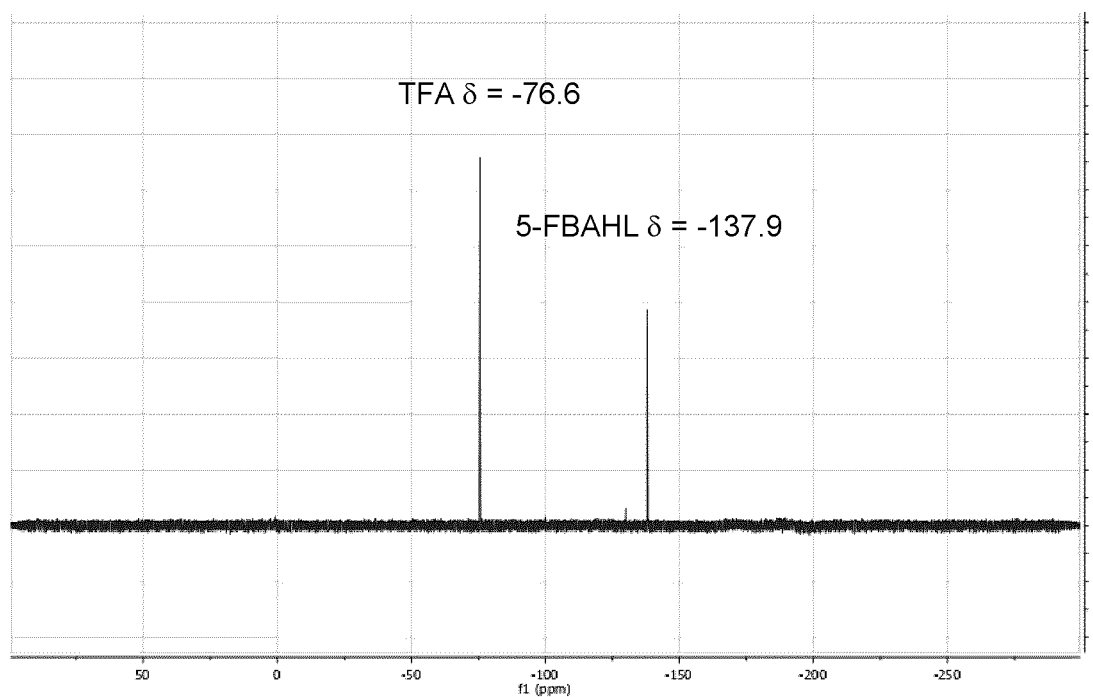
FIG. 13: $^{19}$F NMR spectrum (470 MHz, $D_2O$) of purified 5-[$^{18}$F]FBAHL/β-homoleucine mixture after ~100 h decay at –20° C.

FIG. 13 illustrates the $^{19}$F NMR spectrum (470 MHz, D$_2$O) of purified 5-[$^{18}$F]FBAHL/β-homoleucine mixture after ~100 h decay at −20° C.

Figure 14:
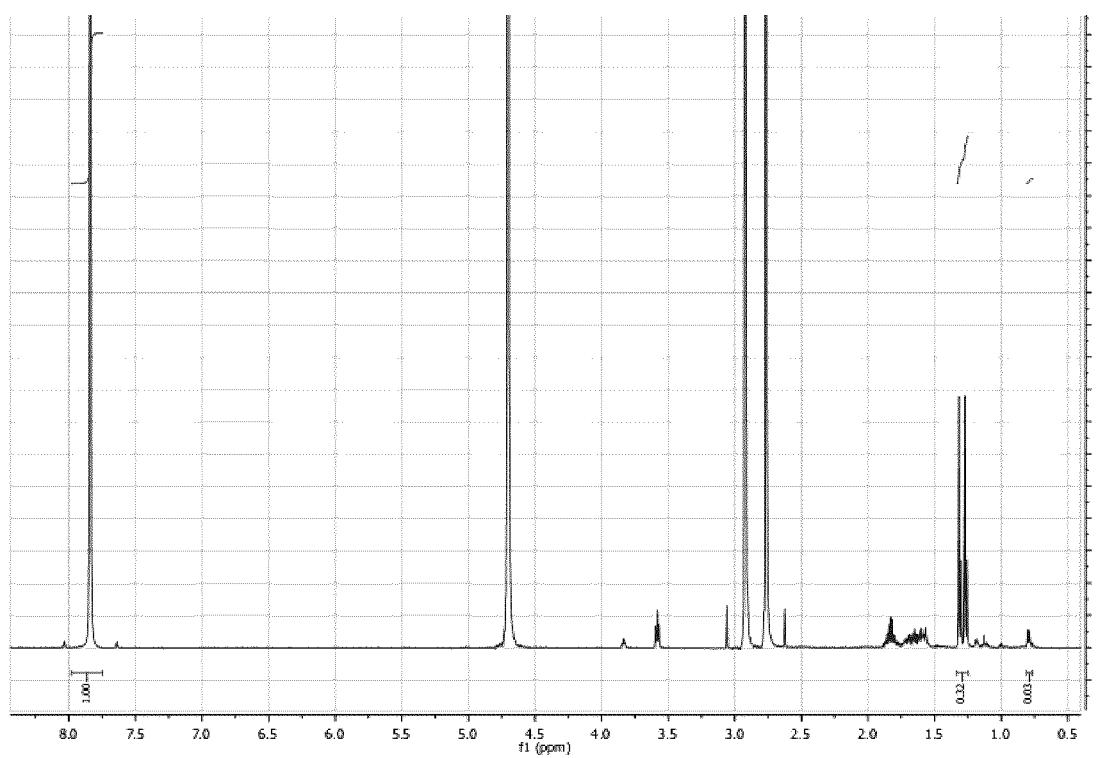
FIG. 14: $^1$H NMR spectrum (500 MHz, $D_2O$) of purified 5-[$^{18}$F]FHL/homoleucine mixture after ~100 h decay at –20° C.

FIG. 14 illustrates the $^1$H NMR spectrum (500 MHz, D$_2$O) of purified 5-[$^{18}$F]FHL/homoleucine mixture after ~100 h decay at −20° C. Doubling of resonances for methyl groups (δ=1.29) are due to the pH of the elution solvent (~8.5).

Figure 15:
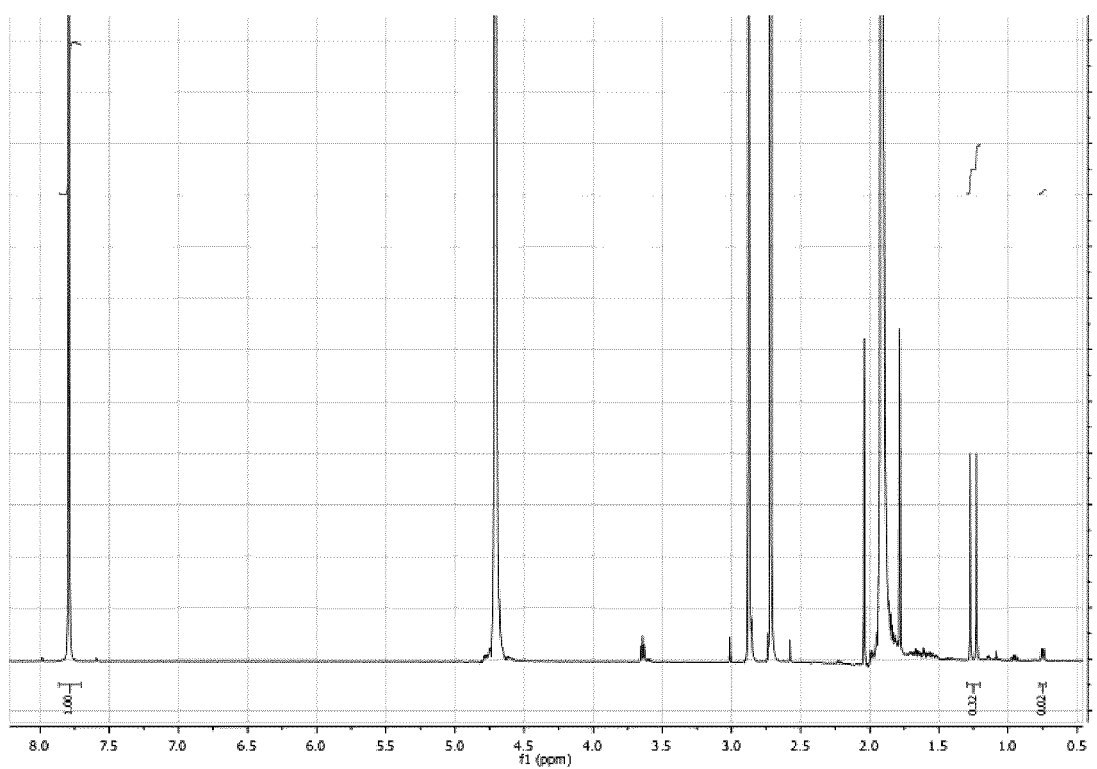
FIG. 15: $^1$H NMR spectrum (500 MHz, $D_2O$) of purified 5-[$^{18}$F]FHL/homoleucine mixture following the addition of AcOH to pH ~4.

FIG. 15 illustrates the $^1$H NMR spectrum (500 MHz, D$_2$O) of the purified 5-[$^{18}$F]FHL/homoleucine mixture following the addition of AcOH to pH ~4.

Figure 16:
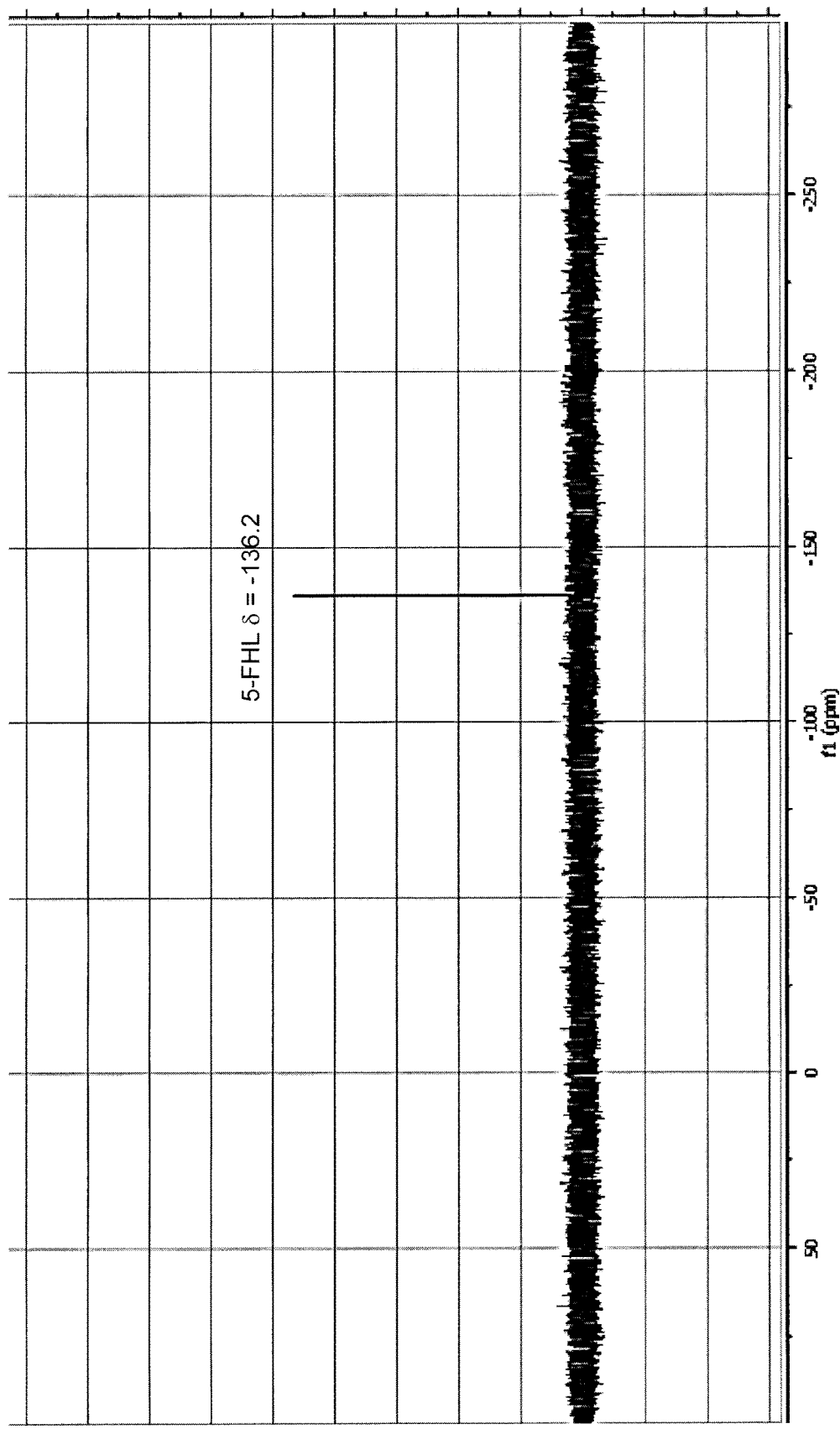
FIG. 16: Typical $^{19}$F NMR spectrum (470 MHz, $D_2O$) of purified 5-[$^{18}$F]FHL/homoleucine mixture after ~100 h decay at –20° C. and following addition of AcOH to pH ~4.

FIG. 16 illustrates the $^{19}$F NMR spectrum (470 MHz, D$_2$O) of purified 5-[$^{18}$F]FHL/homoleucine mixture after ~100 h decay at −20° C. and following addition of AcOH to pH ~4.

Figure 17:
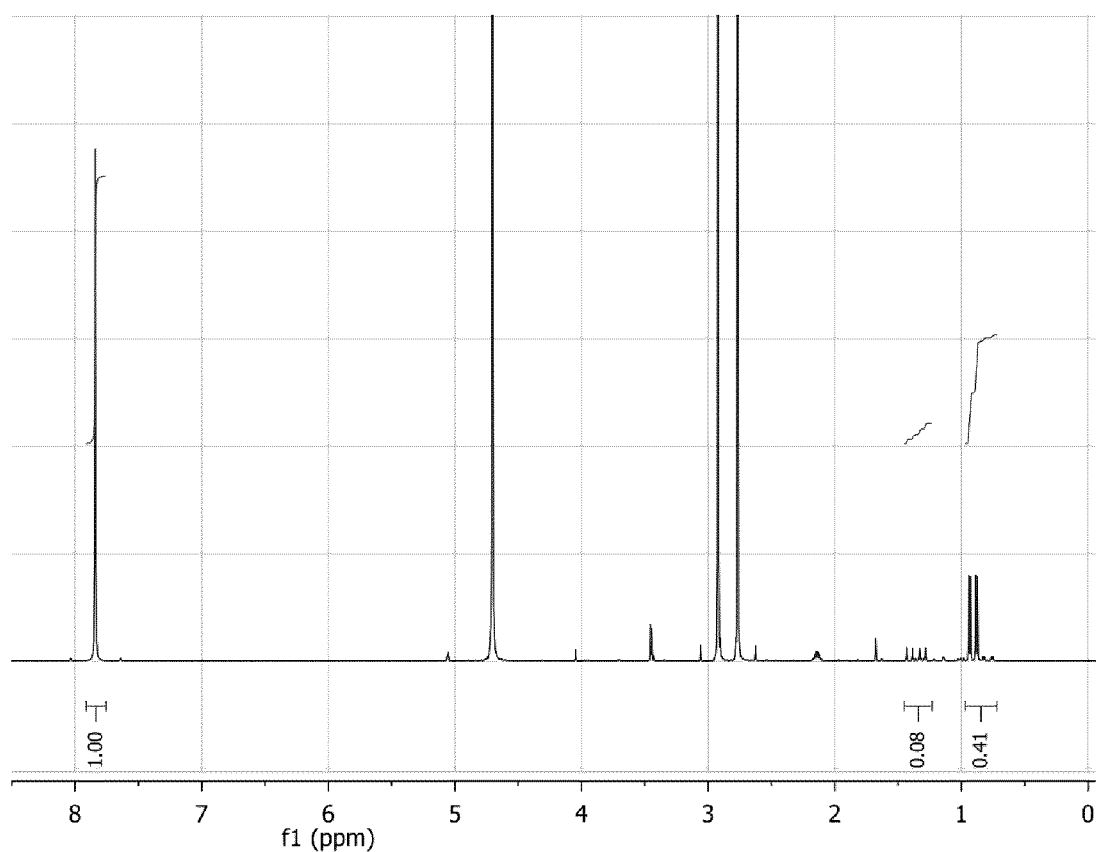
FIG. 17: $^1$H NMR spectrum (500 MHz, D$_2$O) of purified 3-[$^{18}$F]FV/valine mixture after ~100 h decay at −20° C.

FIG. 17 illustrates the $^1$H NMR spectrum (500 MHz, D$_2$O) of purified 3-[$^{18}$F]FV/valine mixture after ~100 h decay at −20° C. Doubling of resonances for methyl groups (δ=0.85, ~1.4) are due to the pH of the elution solvent (~8.5).

Figure 18:
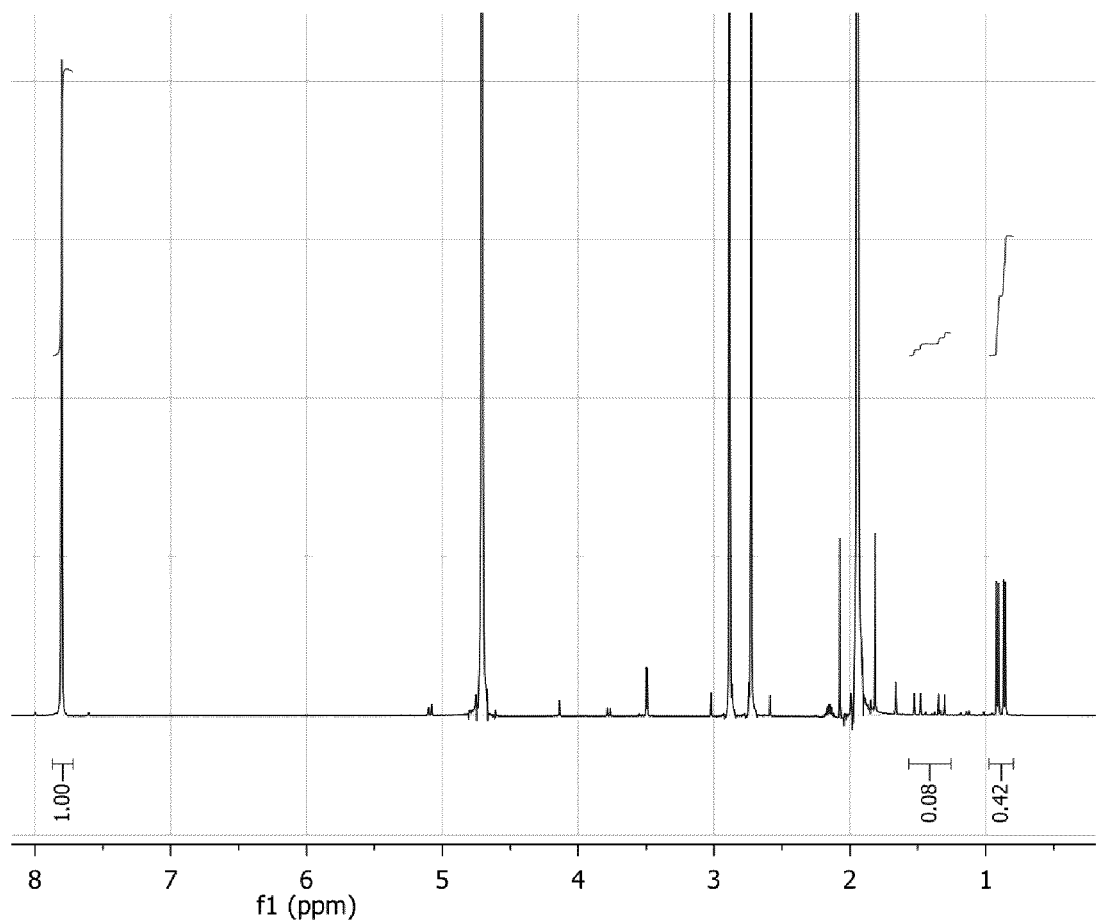
FIG. 18: $^1$H NMR spectrum (500 MHz, D$_2$O) of purified 3-[$^{18}$F]FV/valine mixture following the addition of AcOH to pH ~4.

FIG. 18 illustrates $^1$H NMR spectrum (500 MHz, D$_2$O) of the purified 3-[$^{18}$F]FV/valine mixture following the addition of AcOH to pH ~4.

Figure 19:
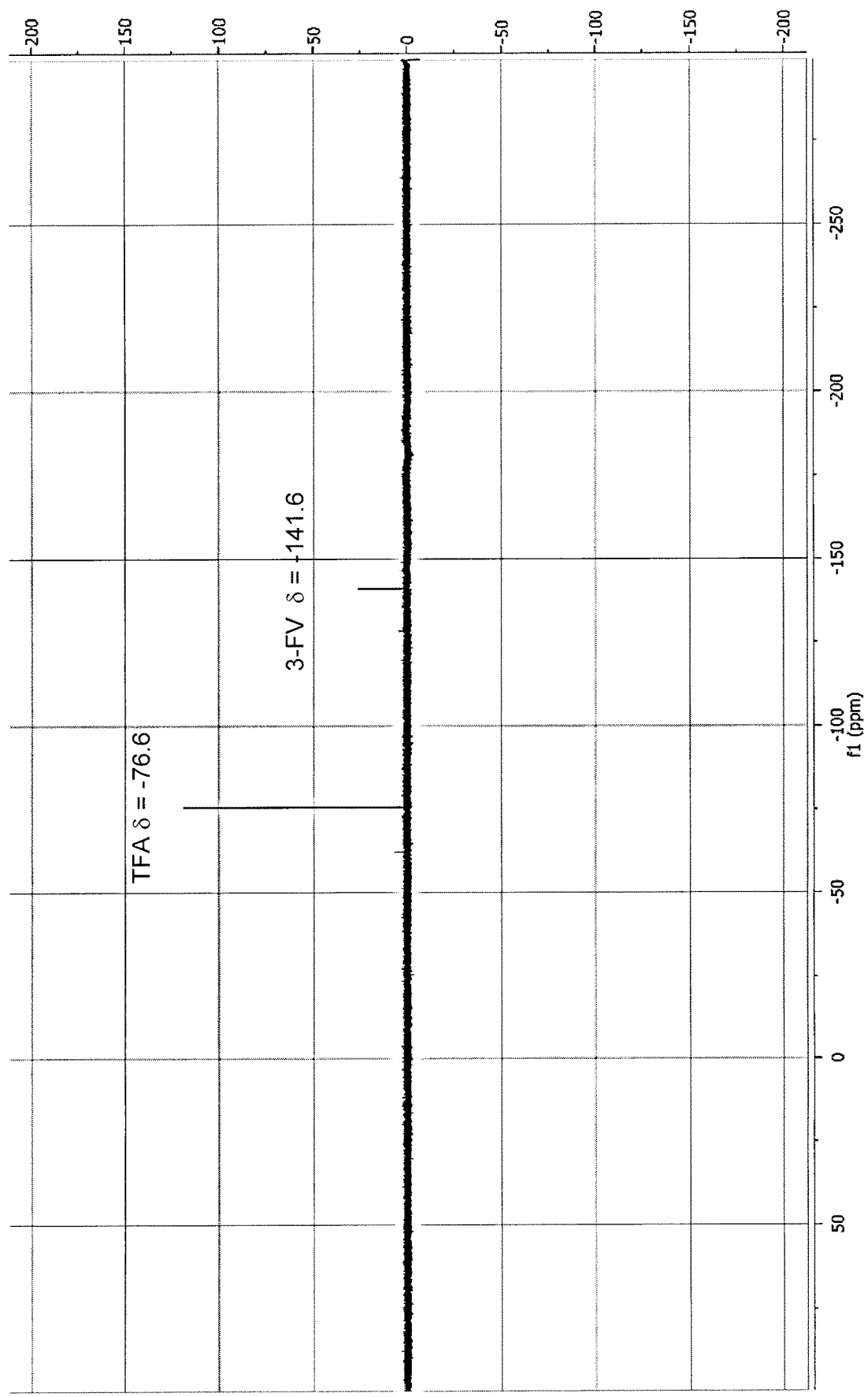
FIG. 19: $^{19}$F NMR spectrum (470 MHz, D$_2$O) of purified 3-[$^{18}$F]FV/valine mixture after ~100 h decay at −20° C. and following addition of TFA to pH ~4.

FIG. 19 illustrates $^{19}$F NMR spectrum (470 MHz, D$_2$O) of purified 3-[$^{18}$F]FV/valine mixture after ~100 h decay at −20° C. and following addition of TFA to pH ~4.

Example 7: Determination of Specific Activity

The radiochemical yield (RCY) is reported as a percentage and represents the total activity present in the purified $^{18}$F-labeled amino acid divided by the total activity present in the purified [$^{18}$F]NFSI×100.

To determine the specific activity (SA) of 4-[$^{18}$F]FL, 5-[$^{18}$F]BAHL, 5-[$^{18}$F]HL and 3-[$^{18}$F]VL the purified product mixtures were eluted from the ion exchange column in 1 mL fractions. Each fraction was counted, then the whole sample was allowed to decay at −20° C. After ~100 h, the fractions were then lyophilized to dryness. Each entire dried fraction was then taken up in D$_2$O and N,N-dimethylformamide (5 μl, 65 μmol) was added as an internal standard. After thorough mixing the $^1$H and $^{19}$F NMR spectra were recorded. Amounts of 4-FL, 5-FBAHL, 5-FHL and 3-VL were determined by analysis of the $^1$H NMR spectra. Specific activity (SA) was then determined by correlating the amount of fluorinated product in each fraction to its activity. SA measurements were determined via at least three independent experiments. As the radiofluorination process described herein does not remove any unreacted amino acid, the effective SA is also calculated a number which takes into account the amounts of fluorinated amino acid as well as amounts of parent amino acid. These values are presented in Table 2:

| Radiotracer | Effective SA (MBq/μmol) |
| --- | --- |
| 4-[$^{18}$F]FL | 3.82 ± 0.91 |
| 5-[$^{18}$F]FBAHL | 2.2 ± 0.50 |
| 5-[$^{18}$F]FHL | 4.92 ± 1.47 |
| 3-[$^{18}$F]FV | 0.43 ± 0.40 |

Example 8 to 10: Synthesis of [$^{18}$F]FDBHL (Compound 11), 4-[$^{18}$F]FαML (Compound 12), and [$^{18}$F]FDL (compound 13)

Compounds 11, 12 and 13 were prepared using photoreactor as shown in FIG. 2, following a general procedure as discussed below:

In particular, sodium dibenzenesulfonamide (40 mg, 124 µmol) was dissolved in 1.1 mL of 4.5:1 CH$_3$CN:H$_2$O and placed in a conical vial. [$^{18}$F]F$_2$ produced in the cyclotron target was then passed through the solution over a period of 15 min. The waste gas was trapped by saturated KI solution. Typically 1-2 GBq was trapped in the reaction mixture. The resulting solution was then passed through a SepPak (Waters tC18 SepPak Plus Long Cartridge). The cartridge was washed with 10 mL H$_2$O followed by 600 µL CH$_3$CN. [$^{18}$F]NFSI was then eluted from the SepPak cartridge in 2.4 mL CH$_3$CN.

Of the 2.4 mL eluent, approx. 1.2 mL (approx. 21 umol), was added to a slurry of substrate: D-BHl-TFA, or FaMeLeu-TFA or D-leucine-TFA (10-15 mg) and sodium decatungstate (NaDT, 5 mg, 2.0 µmol) in 200-400 µL H$_2$O and mixed briefly. The remaining procedure is carried out in a similar manner as discussed in example 3.

Figure 20:
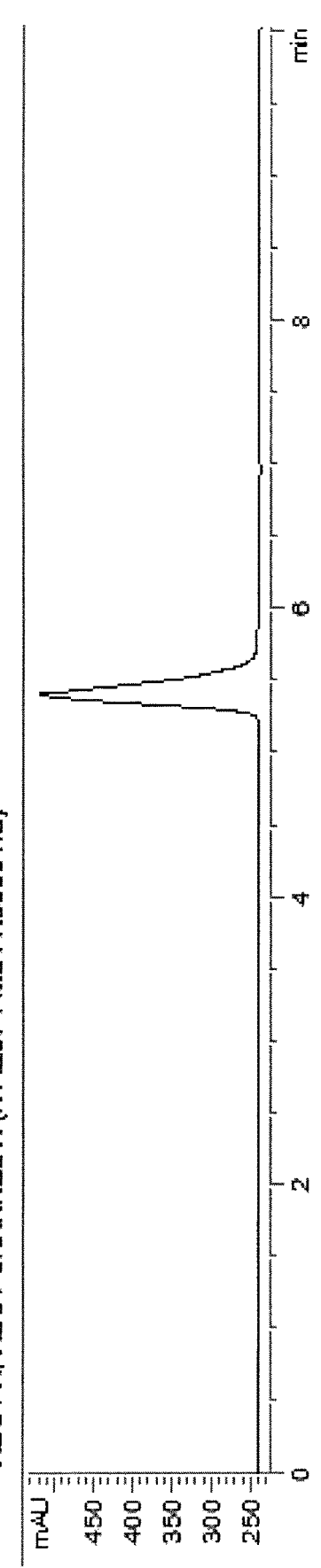
FIG. 20: Radio HPLC gamma traces for radiosynthesis of an exemplary embodiment in accordance with the present invention (i.e. 5-[$^{18}$F]Fα-MeL).

FIG. 20 radiodetected HPLC traces for radiosynthesis of [$^{18}$F]FαMeL (compound 11).

Figure 21:
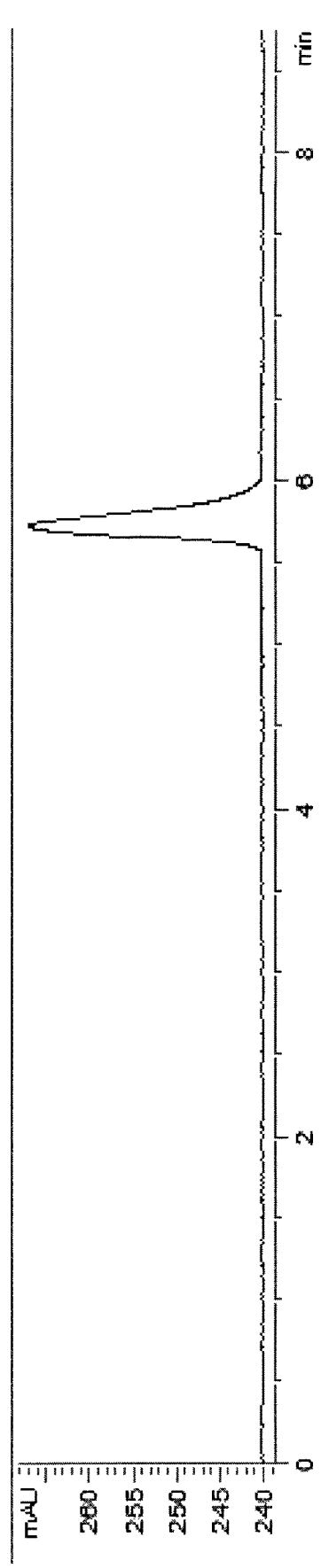
FIG. 21: Radio HPLC gamma traces for radiosynthesis of an exemplary embodiment in accordance with the present invention (i.e. 5-[$^{18}$F]FDBHL).

FIG. 21 radiodetected HPLC traces for radiosynthesis of [$^{18}$F]FDBHL(compound 12).

Figure 22:
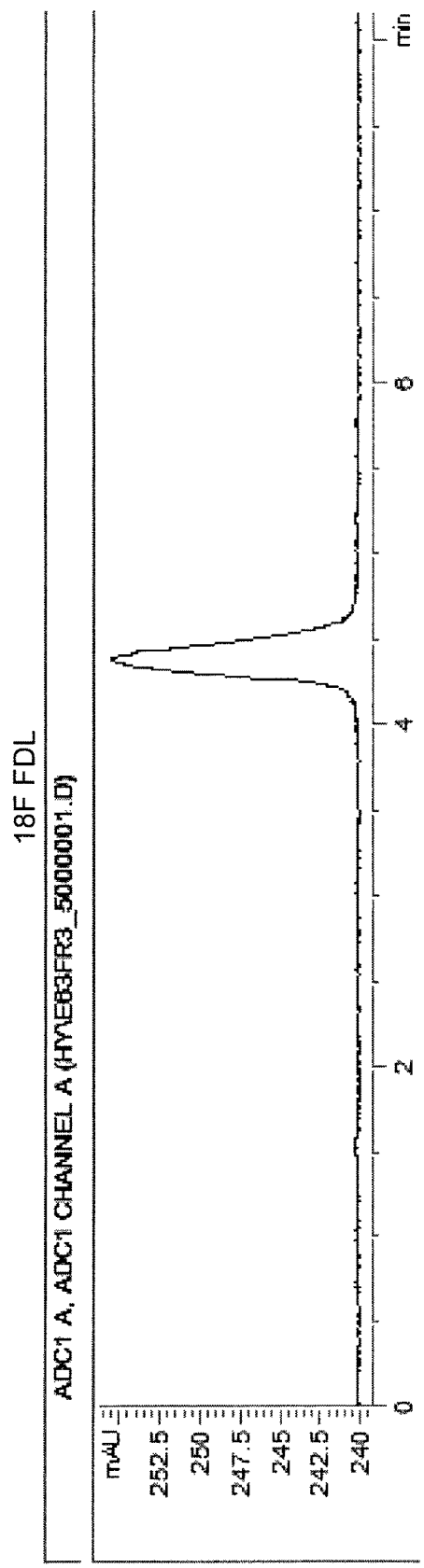
FIG. 22: Radio HPLC gamma traces for radiosynthesis of an exemplary embodiment in accordance with the present invention (i.e. 5-[$^{18}$F]FDL).

FIG. 22 radiodetected HPLC traces for radiosynthesis of [$^{18}$F]FDL(compound 13).

Example 11: Synthesis of [$^{18}$F]FPregab (Compound 14)

[$^{18}$F]FPregab was prepared using a photoreactor as shown in FIG. 3, following the following procedure as discussed in Example 6.

Figure 23:
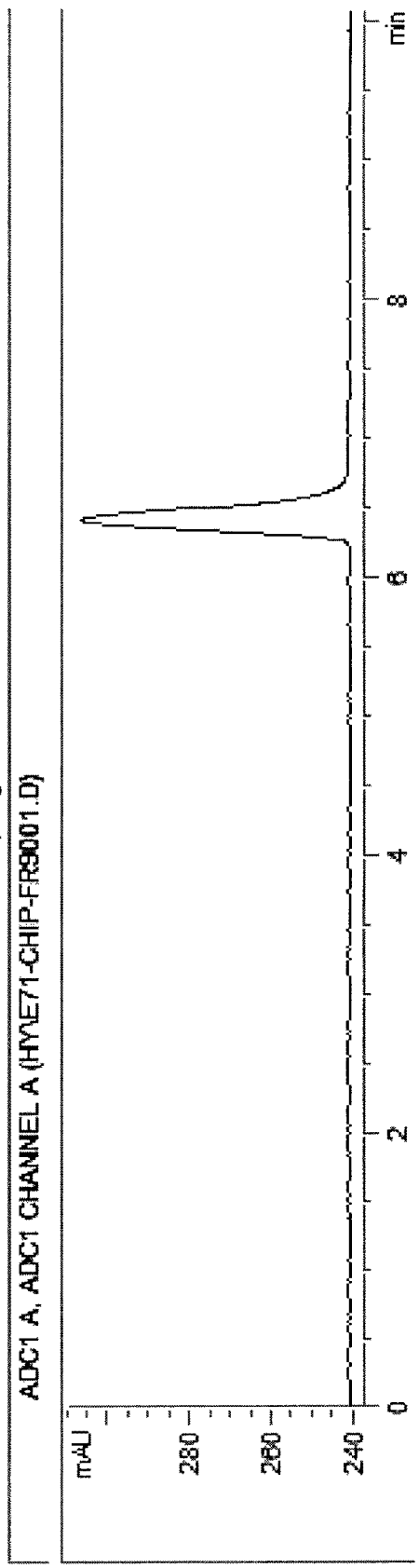
FIG. 23: Radio HPLC gamma traces for radiosynthesis of an exemplary embodiment in accordance with the present invention (i.e. 5-[$^{18}$F]pregabalin).

FIG. 23 illustrates the HPLC traces of [$^{18}$F]FPregab (compound 14).

Examples 12 to 17: Synthesis of [$^{18}$F]KL (Compound 15), [$^{18}$F]NL (Compound 16), [$^{18}$F]PSMA EHle(F) (compound 17)

The above exemplary compounds 15, 16, and 17 were prepared by the following general procedure.

[$^{18}$F]NFSI was prepared in a same manner as described for examples 8-11. The [$^{18}$F]NFSI solution was split into two parts for two reactions, added to a slurry of the substrate H-KL-OH.2TFA (25.7 mg, 53 µmol), or H-NL-OH.2TFA (25.4 mg, 54 µmol), or PSMA EHle (20.2, 63 µmol) and sodium decatungstate (NaDT, 5 mg, 2.0 mol) in 200 µL H2O and mixed briefly (heat for a while to fully dissolve if the mixture was not clear). The solution was then loaded onto the photoreactor as show in FIG. 2 and irradiated for 40 min After this time the solution was removed and the PTFE tube was washed with CH$_3$CN (1 mL). A fraction of the resulting mixture was subjected to HPLC analysis to get the radiochemical conversion (RCC). The resulting solution was loaded onto a preconditioned strong cation exchange cartridge (Silicycle, 500 mg resin) and the cartridge was washed with CH$_3$CN (10 mL) followed by H$_2$O (10 mL). [$^{18}$F]KL(F), [$^{18}$F]NL(F), [$^{18}$F]PSMA EHle(F) were then eluted from the cartridge with 1.5 mL aliquots of 150 mM NaHCO$_3$, yielding a mixture of fluorinated product and starting material. The bulk of the activity was typically eluted in the 3th and 4th 1.5 mL aliquot. Analytical HPLC was carried out on a Phenomenex Luna C18 (4.6×100 mm, 1 mL/min) using a gradient of 100% solvent A (0.1% TFA in H$_2$O) to 100% solvent B (0.1% TFA in CH$_3$CN) over 15 min. The radiochemical yield (RCY) is reported as a percentage and represents the total activity present in the purified $^{18}$F-labeled amino acid divided by the total activity present in the purified [$^{18}$F]NFSI×100 (decay corrected).

5-[$^{18}$F]KL (compound 15) produced using the above method exhibit a specific activity of 2.32 MBq/µmol (n=1), radiochemical purity of >95%, radiochemical yield of 24%±3% (n=4), and radiochemical conversion of 35%±4% (n=4)).

[$^{18}$F]NL (compound 16) produced using the above method exhibit a specific activity of 2.4 MBq/µmol (n=1), radiochemical purity of >95%, radiochemical yield of 40%±4% (n=4), and radiochemical conversion of 51%±5% (n=4).

[$^{18}$F]PSMA EHle(F) (compound 17) produced using this method has radiochemical purity of 71%, radiochemical yield of 9%; and radiochemical conversion of 1-2%.

Figure 24:
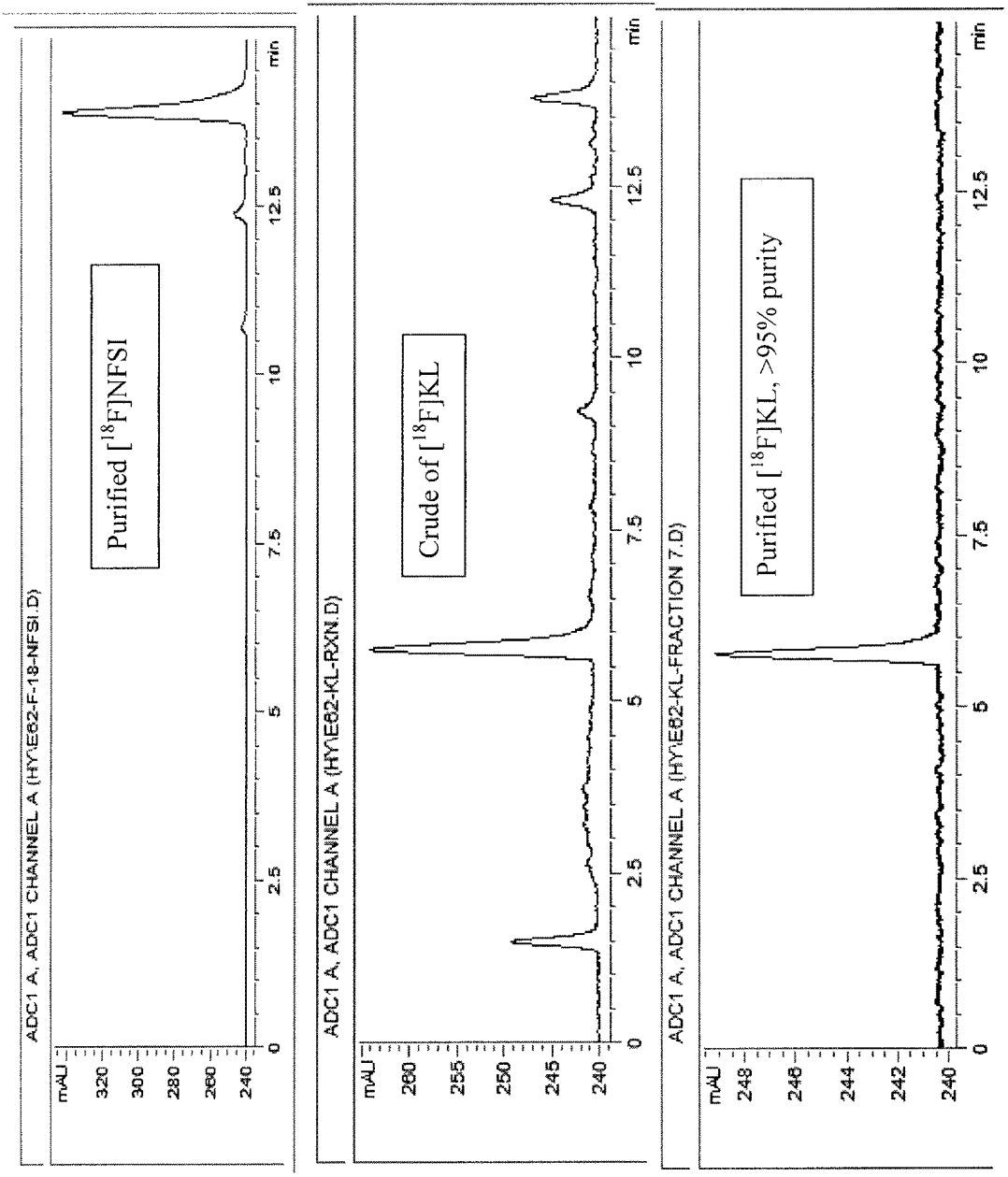
FIG. 24: Radiodetected HPLC traces for radiosynthesis of an exemplary embodiment in accordance with the present invention (i.e. [$^{18}$F]KL(F)).

FIG. 24 illustrates radiodetected HPLC traces for radiosynthesis of [$^{18}$F]KL(F) (compound 15).

Figure 25:
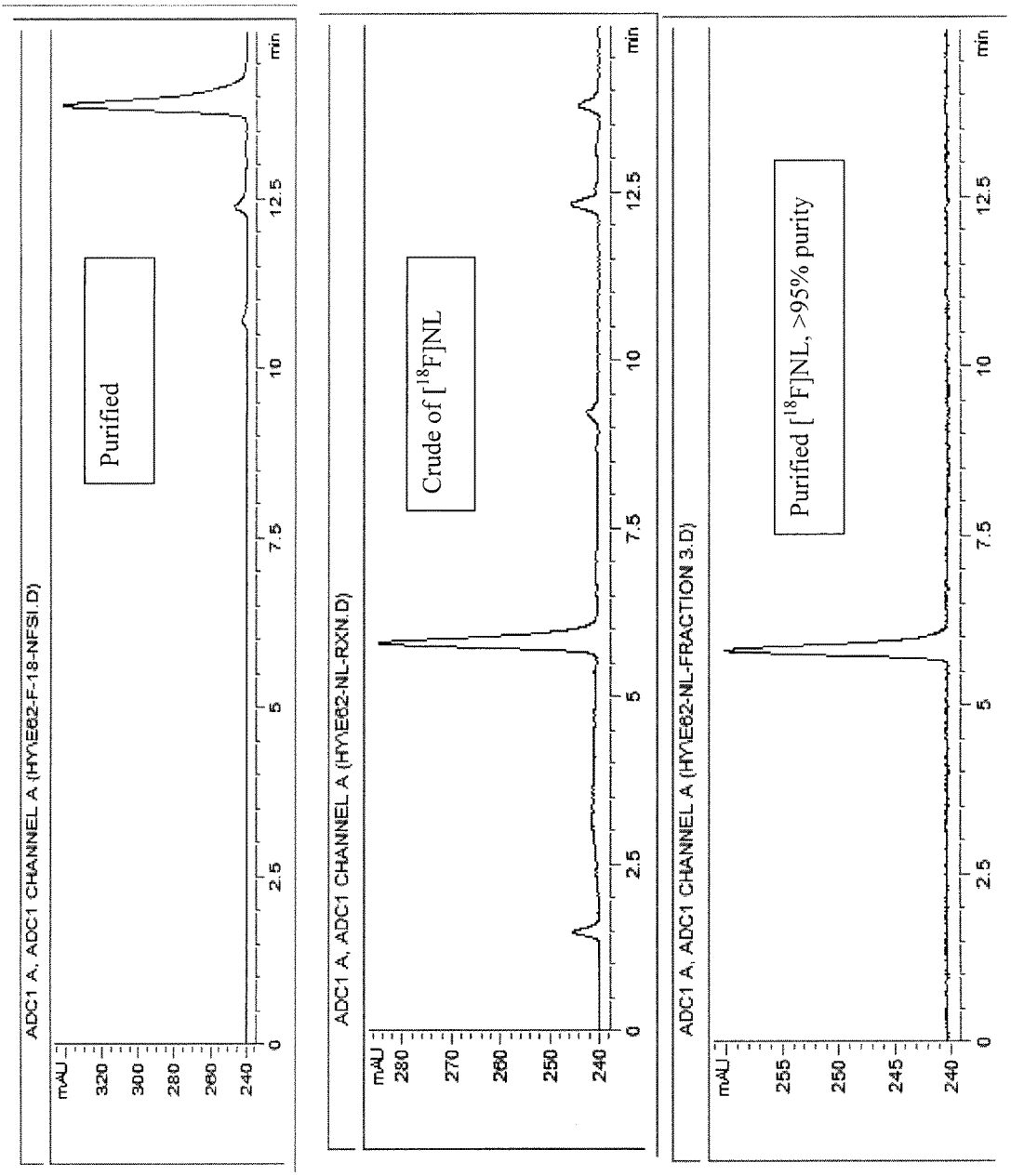
FIG. 25: Radiodetected HPLC traces for radiosynthesis of an exemplary embodiment in accordance with the present invention (i.e. [$^{18}$F]NL(F)).

FIG. 25 illustrates radiodetected HPLC traces for radiosynthesis of [$^{18}$F]NL(F) (compound 16).

Figure 26:
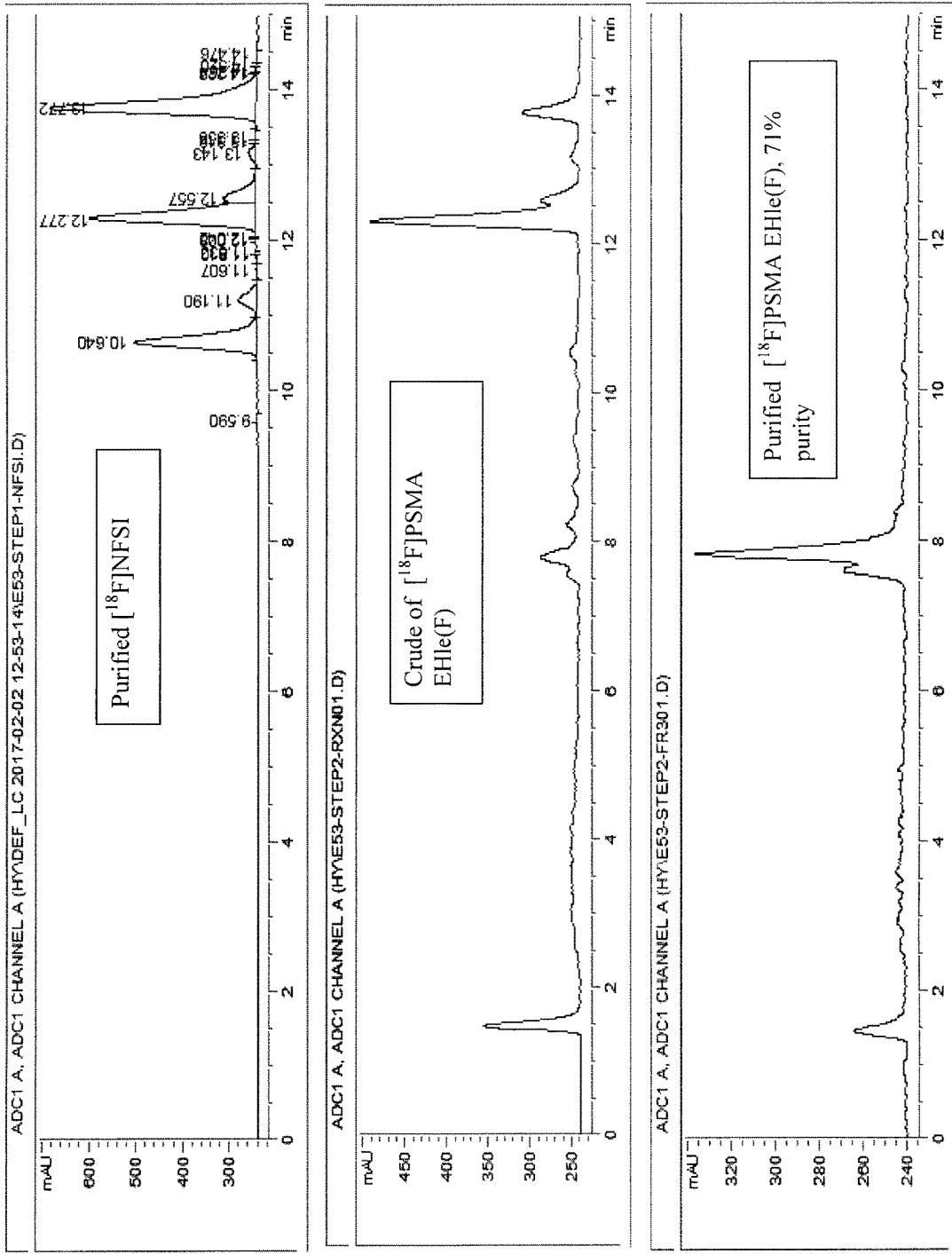
FIG. 26: Radiodetected traces for radiosynthesis of an exemplary embodiment in accordance with the present invention (i.e. [$^{18}$F]PSMA EHle(F)).

FIG. 26 illustrates radiodetected traces for radiosynthesis of [$^{18}$F]PSMA EHle(F) (compound 17).

Examples 18 to 21: Synthesis of [$^{18}$F]GLKA(F) (Compound 18), [$^{18}$F]ELAF(F) (Compound 19), [$^{18}$F]AELG(F) (compound 20), [$^{18}$F]FAEGEA(F) (compound 21)

[$^{18}$F]NFSI was prepared in a same manner as described for examples 8-11. The [$^{18}$F]NFSI solution was split into three parts for three reactions, added to a slurry of the substrate H-GLKA-OH.2TFA (20.7 mg, 34 µmol), H-ELAF-OH.TFA (20.7 mg, 35 µmol), H-AELG-OH.TFA (18.2 mg, 36 µmol), H-FALGEA-NH$_2$.TFA (25.7 mg, 36 µmol), and sodium decatungstate (NaDT, 5 mg, 2.0 µmol) in 200 µL H$_2$O (for H-AELG-OH.TFA 400 µL H2O) and mixed briefly (heat for a while to fully dissolve if the mixture was not clear). The solution was then loaded onto the photoreactor of FIG. 2 or 3, and irradiated for 40 min After this time the solution was removed and the photoreactor was washed with CH$_3$CN (3 mL). A fraction of the resulting mixture was subjected to HPLC analysis to get the radiochemical conversion (RCC). Analytical HPLC was carried out on a Phenomenex Luna C18 (4.6×100 mm, 1 mL/min) using a gradient of 100% solvent A (0.1% TFA in H$_2$O) to 100% solvent B (0.1% TFA in CH$_3$CN) over 15 min. A fraction of 100 µL reaction mixture was used for the purification, after dilution with a solution of 0.1% TFA in H$_2$O (400 mL), the mixture was subjected to semi-preparatory HPLC purification. Semi-preparatory HPLC condition: Phenomenex Luna C18 (4.6×100 mm, 1 mL/min) using a gradient of 100% solvent A (0.1% TFA in H$_2$O) to 100% solvent B (0.1% TFA in CH$_3$CN) over 15 min. The radiochemical yield (RCY) is reported as a percentage and represents the total activity present in the purified $^{18}$F-labeled amino acid divided by the total activity present in the purified [$^{18}$F]NFSI×100 (decay corrected).

[$^{18}$F]GLKA (compound 18) was produced using the above method with the photoreactor of FIG. 3 with a radiochemical conversion of 26%±2% (n=3).

[$^{18}$F]ELAF (compound 19) produced using the above method with the photoreactor of FIG. 2 had radiochemical purity of >95%, radiochemical yield of 23.2%±3% (n=1), and radiochemical conversion of about 26% (n=1). (Compound 18) produced using the above method with the photoreactor of FIG. 3 exhibit a specific activity of 1.32 MBq/µmol (±0.2 MBq/µmol, n=2), radiochemical purity of >95%, radiochemical yield of 25% (±0.3%), and radiochemical conversion of 34% (±1%).

[$^{18}$F]AELG (compound 20) produced using the above method with the photoreactor of FIG. 2 had radiochemical purity of >95%, radiochemical yield of 36.6% (n=1), and radiochemical conversion of about 45±4% (n=3).

Figure 27:
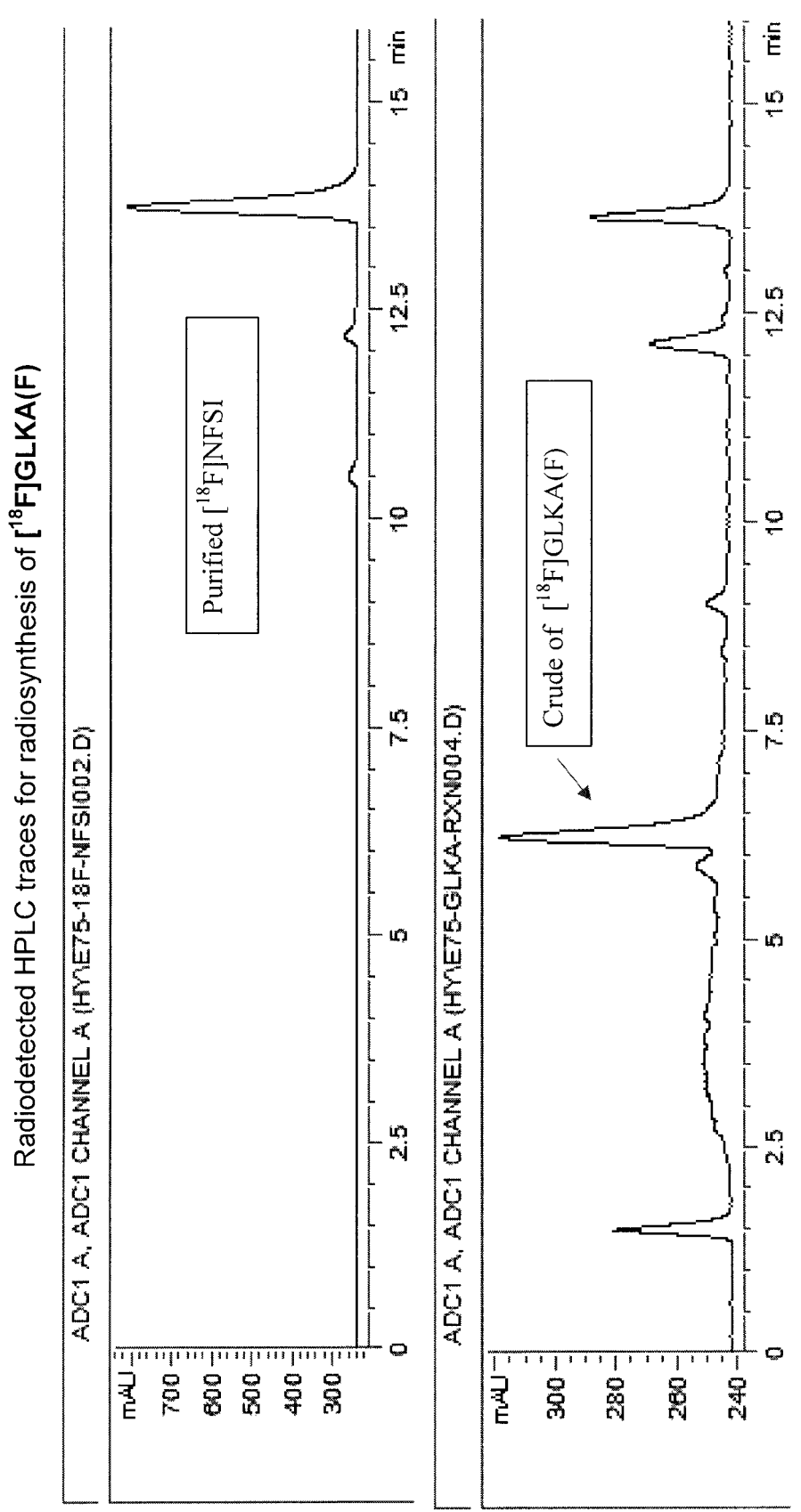
FIG. 27: Radiodetected HPLC traces for radiosynthesis of an exemplary embodiment in accordance with the present invention (i.e. [$^{18}$F]GLKA(F)).

FIG. 27 illustrates radiodetected HPLC traces for radiosynthesis of [$^{18}$F]GLKA(F) (compound 18).

Figure 28:
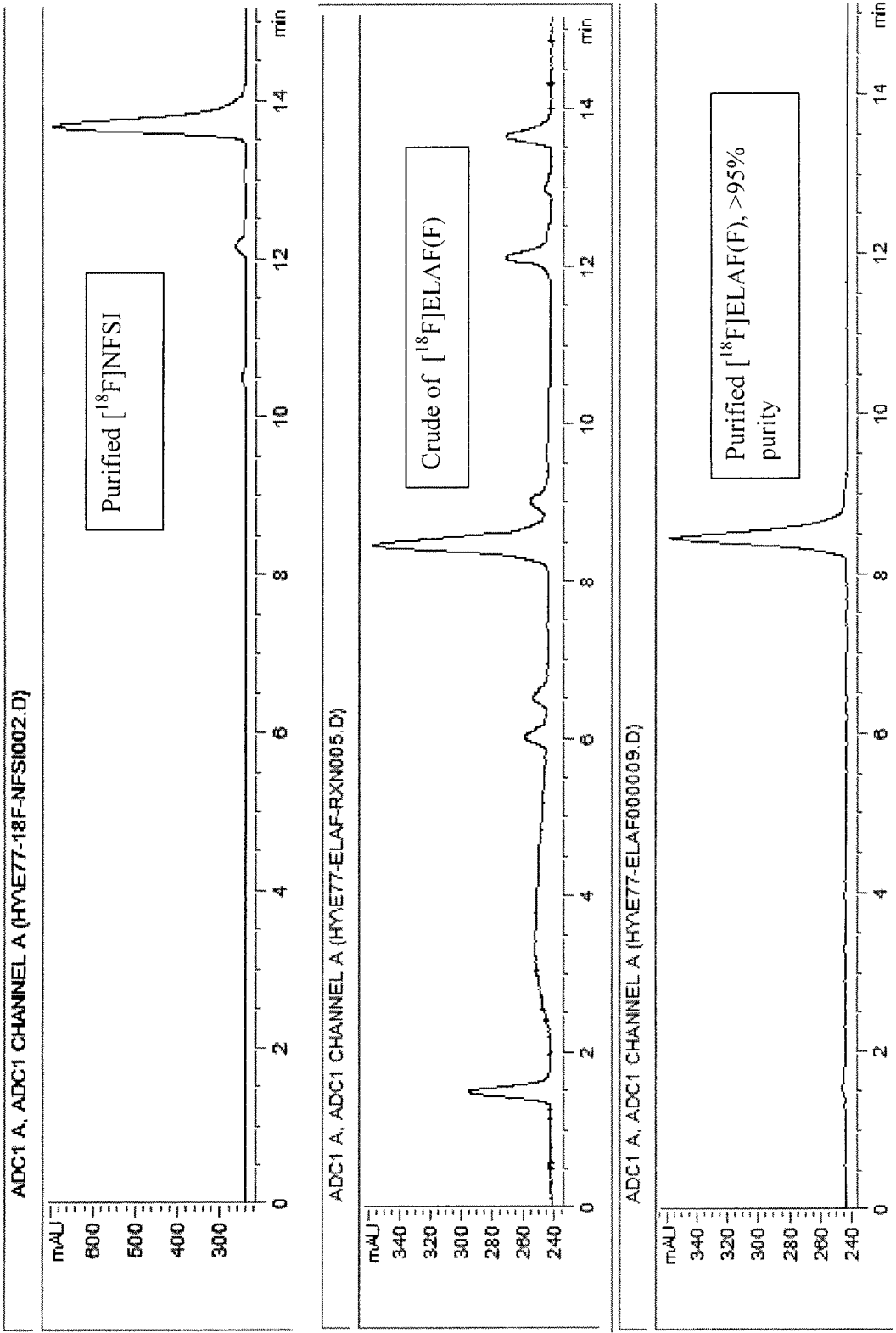
FIG. 28: Radiodetected HPLC traces for radiosynthesis of an exemplary embodiment in accordance with the present invention (i.e. [$^{18}$F]ELAF(F)).

FIG. 28 illustrates radiodetected HPLC traces for radiosynthesis of [$^{18}$F]ELAF(F) (compound 19).

Figure 29:
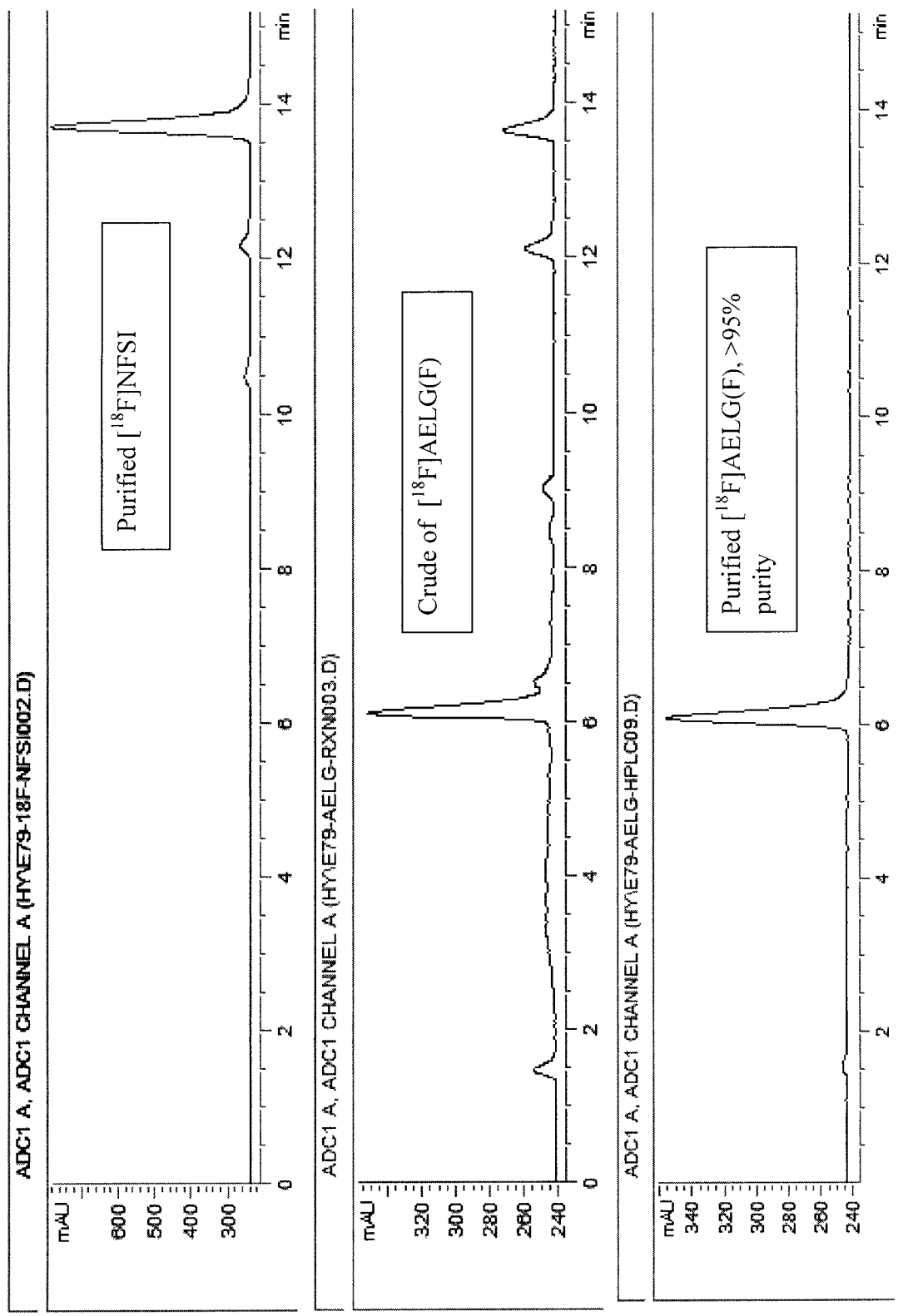
FIG. 29: Radiodetected HPLC traces for radiosynthesis of an exemplary embodiment in accordance with the present invention (i.e. [$^{18}$F]AELG(F)).

FIG. 29 illustrates radiodetected HPLC traces for radiosynthesis of [$^{18}$F]AELG(F) (compound 20).

Figure 30:
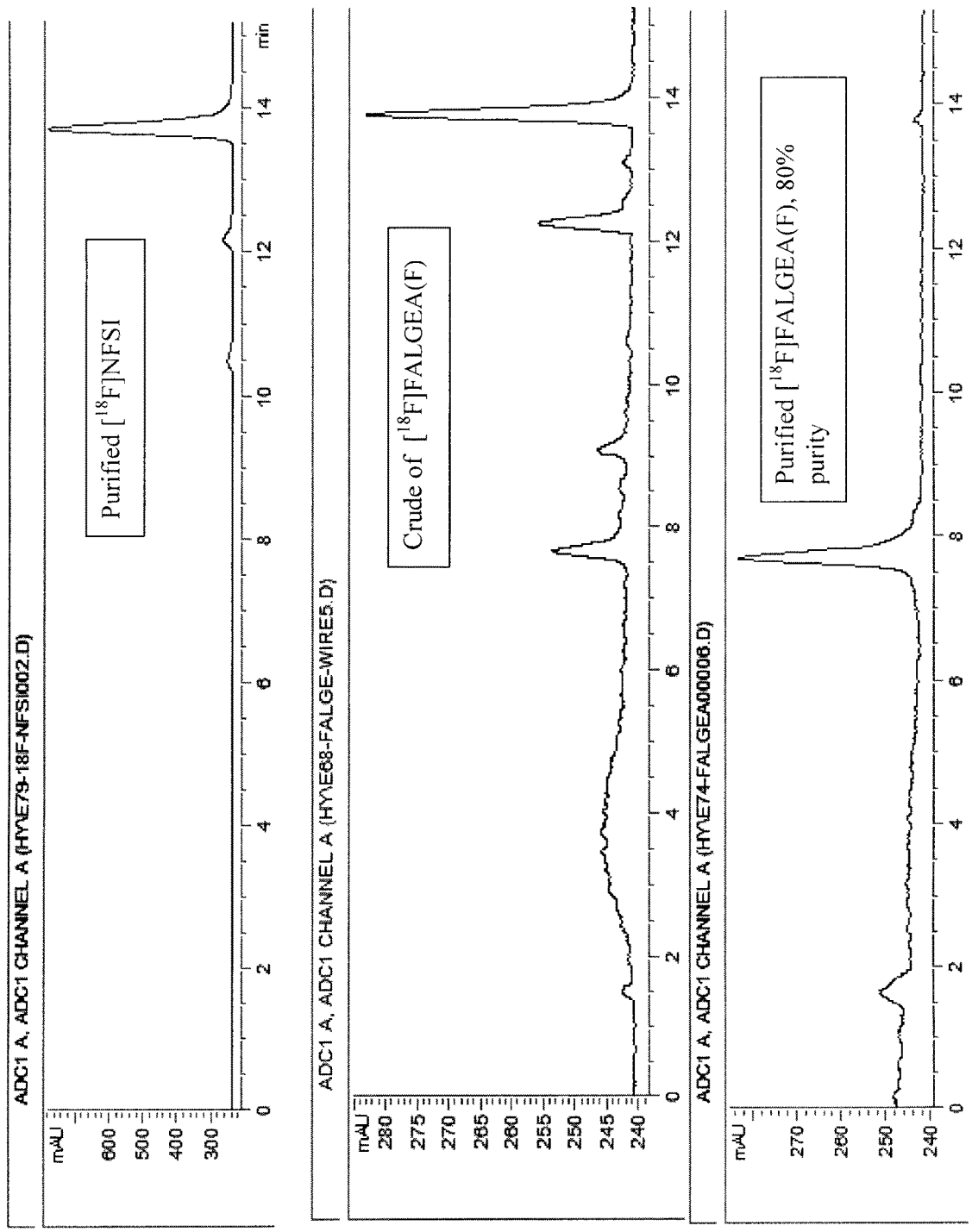
FIG. 30: Radiodetected HPLC traces for radiosynthesis of an exemplary embodiment in accordance with the present invention (i.e. [$^{18}$F]FALGEA(F)).

FIG. 30 illustrates radiodetected HPLC traces for radiosynthesis of [$^{18}$F]ALGEA(F) (compound 21).

Example 22: Determination of Specific Activity

To determine the specific activity (SA) of [$^{18}$F]KL(F), [$^{18}$F]NL(F) the purified product mixtures were eluted from the ion exchange column in 1.5 mL fractions. Each fraction was counted, then the whole sample was allowed to decay at −20° C. To determine the specific activity (SA) of [$^{18}$F]ELAF(F), [$^{18}$F]AELG(F), the HPLC purified product mixtures was allowed to decay at −20° C. After ~100 h, the fractions were then lyophilized to dryness. Each entire dried fraction was then taken up in D$_2$O and N,N-dimethylformamide (5 μmol) was added as an internal standard. Amounts of KL(F), NL(F), ELAF(F) and AELG(F) were determined by analysis of the 1H NMR spectra. Specific activity was then determined by correlating the amount of fluorinated product in each fraction to its activity. SA measurements were determined via at least three independent experiments. As the radiofluorination process described in this report does not remove any unreacted amino acid, we have also calculated the effective SA (for NL and KL)—a number which takes into account the amounts of fluorinated amino acid as well as amounts of parent amino acid.

Figure 31:
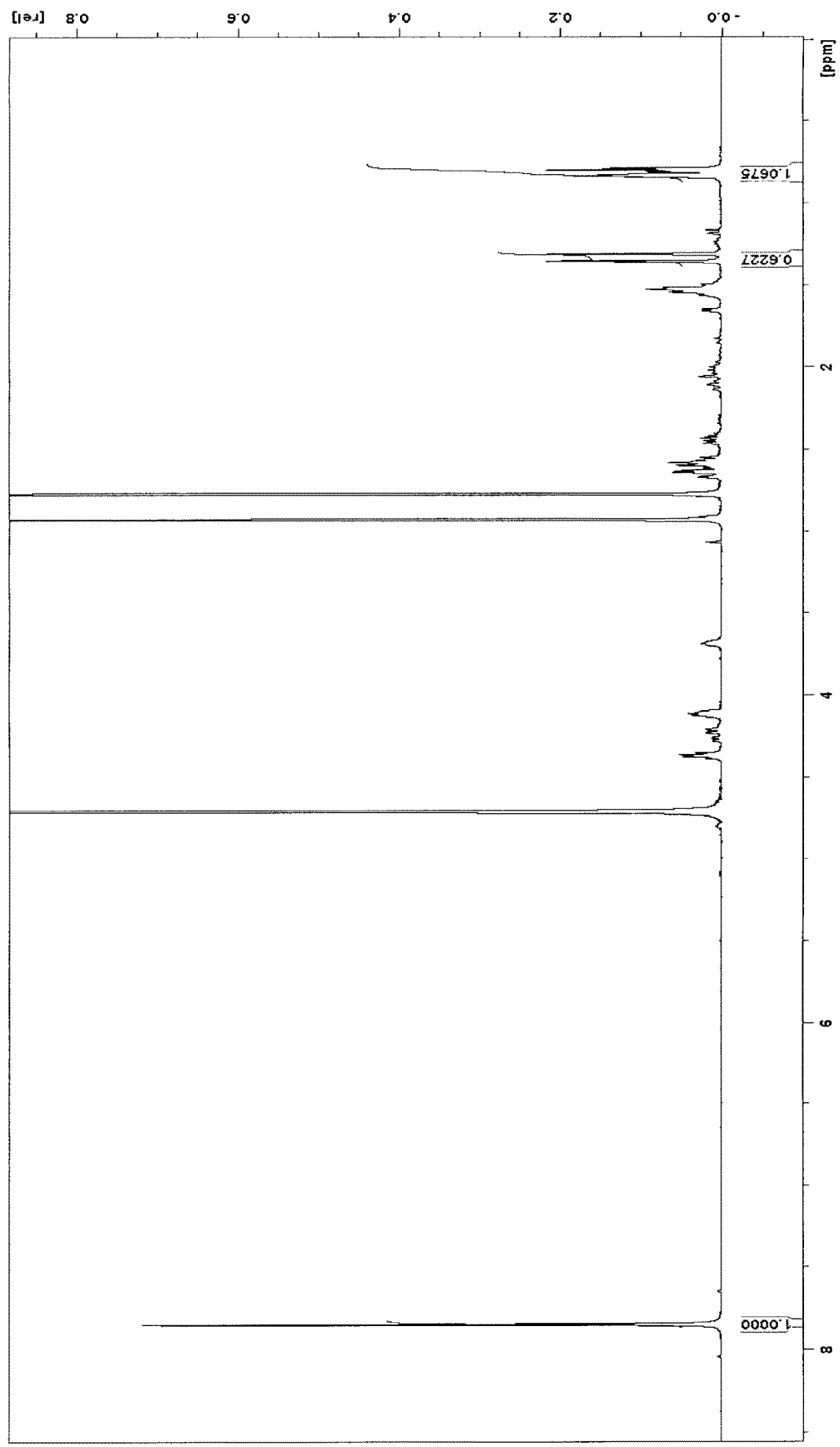
FIG. 31: $^1$H NMR spectrum (500 MHz, D$_2$O) of purified [$^{18}$F]NL(F)/NL after ~100 h decay at −20° C.

FIG. 31 illustrates $^1$H NMR spectrum (500 MHz, D$_2$O) of purified [$^{18}$F]NL(F)/NL after ~100 h decay at −20° C.

Figure 32:
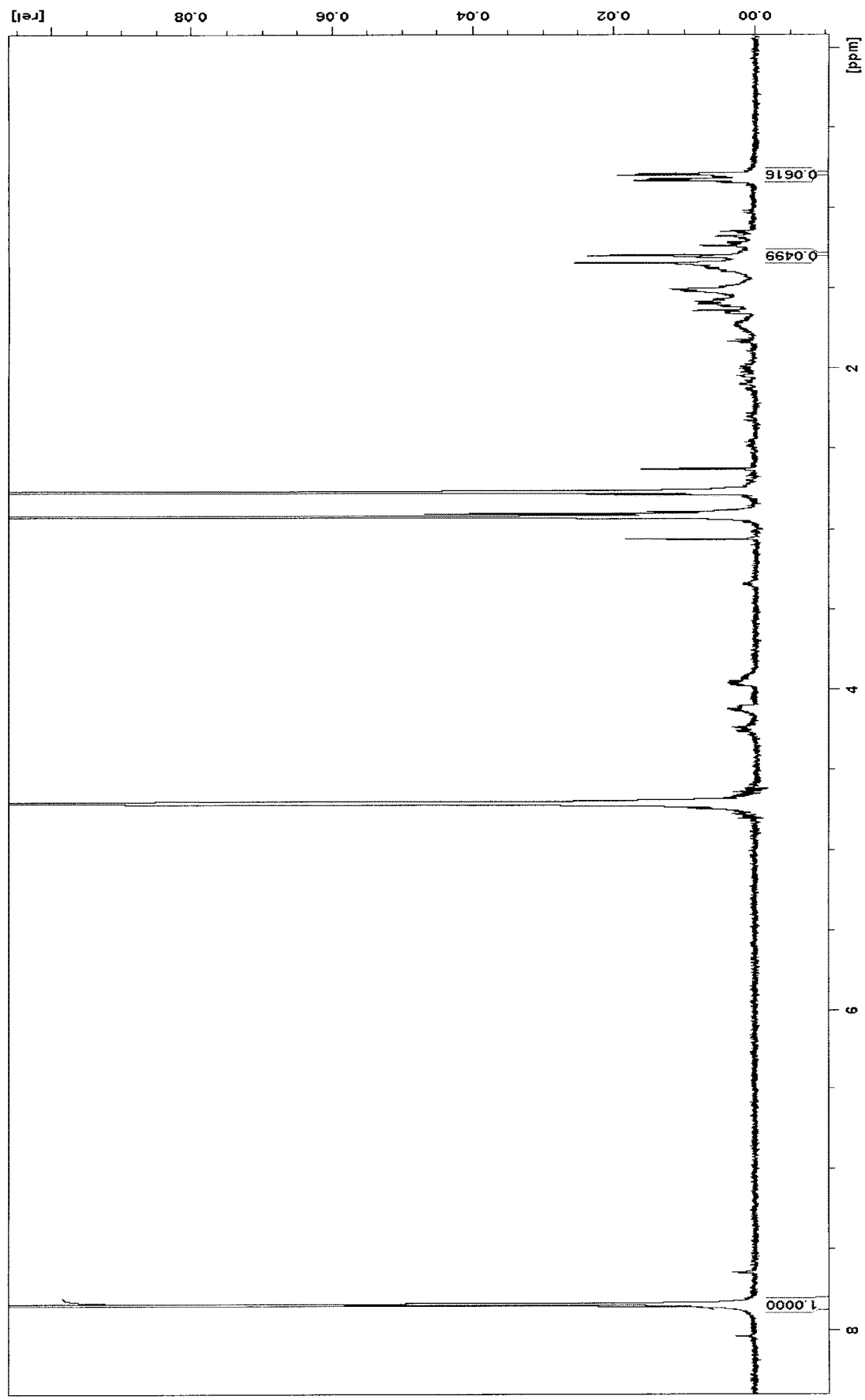
FIG. 32: $^1$H NMR spectrum (500 MHz, D$_2$O) of purified [$^{18}$F]KL(F)/KL after ~100 h decay at −20° C.

FIG. 32 illustrates $^1$H NMR spectrum (500 MHz, D$_2$O) of purified [$^{18}$F]KL(F)/KL after ~100 h decay at −20° C.

Figure 33:
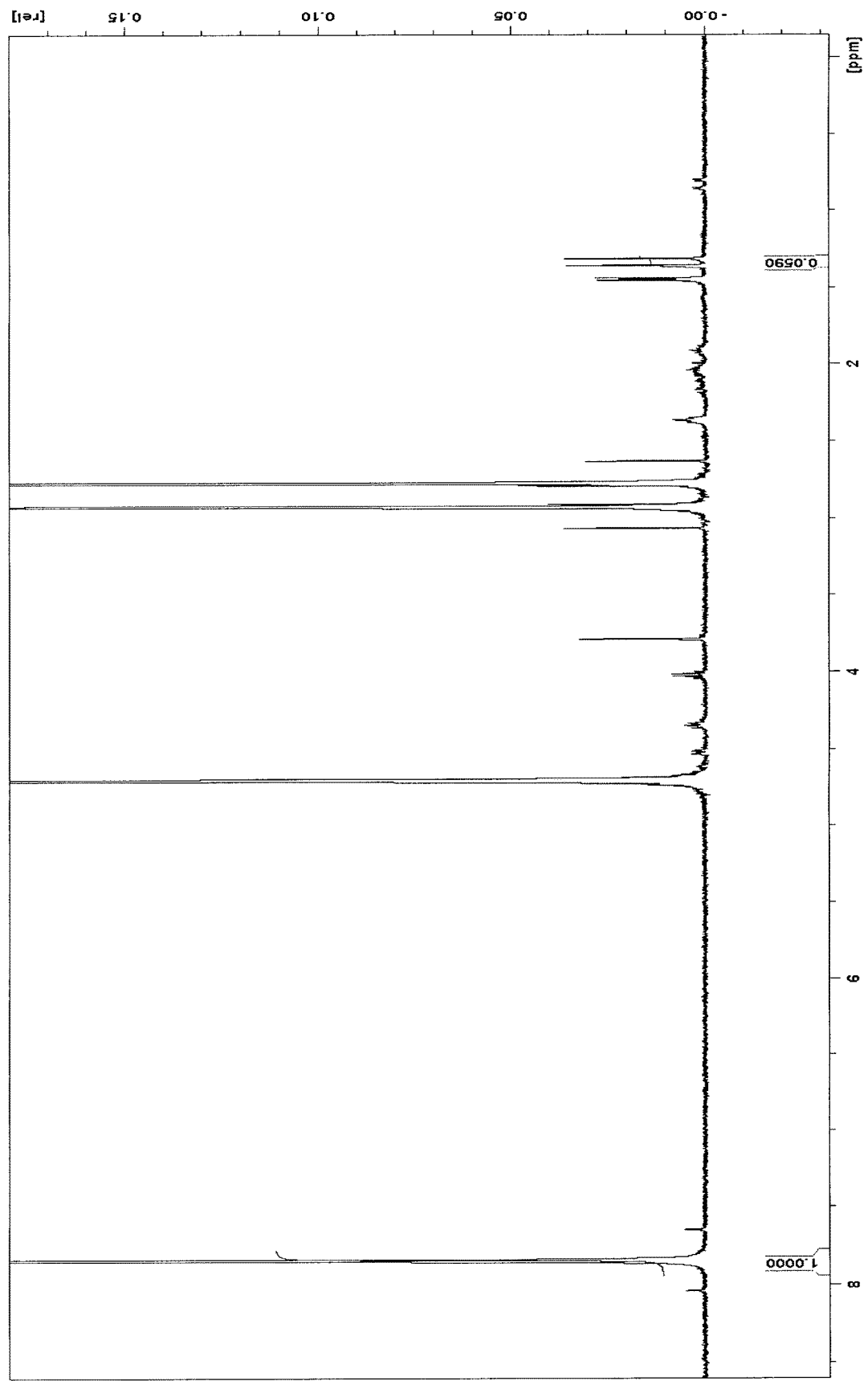
FIG. 33: $^1$H NMR spectrum (500 MHz, D$_2$O) of purified [$^{18}$F]AELG(F) after ~100 h decay at −20° C.

FIG. 33 illustrates $^1$H NMR spectrum (500 MHz, D$_2$O) of purified [$^{18}$F]AELG(F) after ~100 h decay at −20° C.

Figure 34:
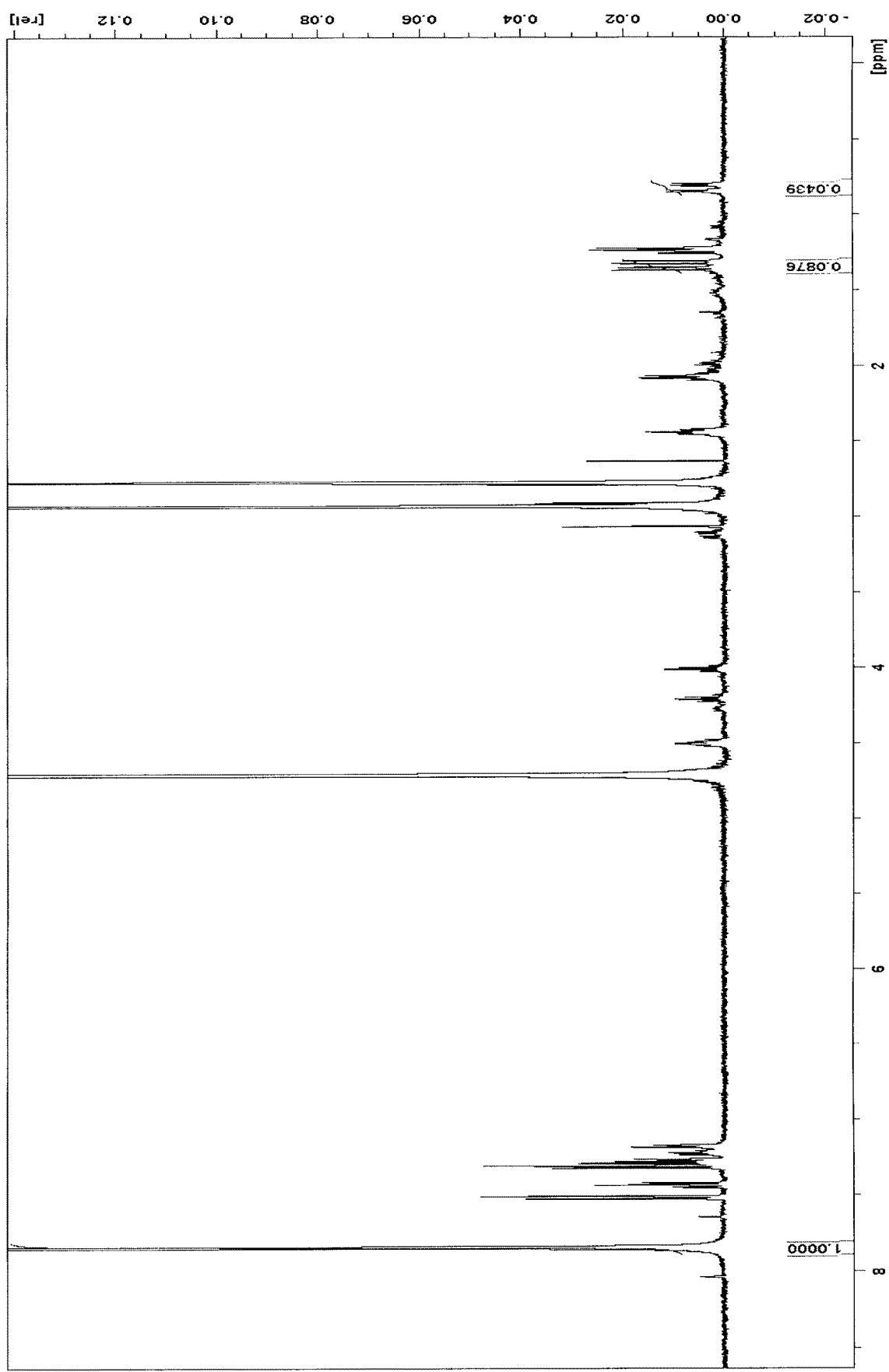
FIG. 34 illustrates $^1$H NMR spectrum (500 MHz, D$_2$O) of purified [$^{18}$F]ELAF(F)/ELAF after ~100 h decay at −20° C.

FIG. 34 illustrates $^1$H NMR spectrum (500 MHz, D$_2$O) of purified [$^{18}$F]ELAF(F)/ELAF after ~100 h decay at −20° C.

B) Activity Testing

Example 23: Cell Uptake Studies

The LNCaP and PC-3 cell lines were obtained from ATCC. MCF-7 were obtained as a gift from Dr. C. K. Osborne (Houston, Tex.). All cell lines were authenticated by short tandem repeat (STR) profiling. Briefly, the cells were seeded in 24-well plates until approximately 90% confluence, and a fixed amount (74 kBq) of radioactive tracer (4-[$^{18}$F]FL or 5-[$^{18}$F]FHL) was added to each well. The cells were incubated with the radiotracer at 37° C. for 20, 40 and 60 minutes with gentle agitation. Blocking experiments were performed using 10 mM 2-amino-2-norbornanecarboxylic (BCH), a blocker of L-amino acid transport. Following incubation, each well was washed with ice-cold Hepes buffer. Replicate wells were used for cell counting. The cells were lysed with 1 M NaOH. The activity in supernatant, washes and cell lysates was measured using a PerkinElmer Wizard 2480 gamma counter. The activity is reported as the percentage of incubated activity, and cellular uptake was normalized to cell number.

Figure 35:
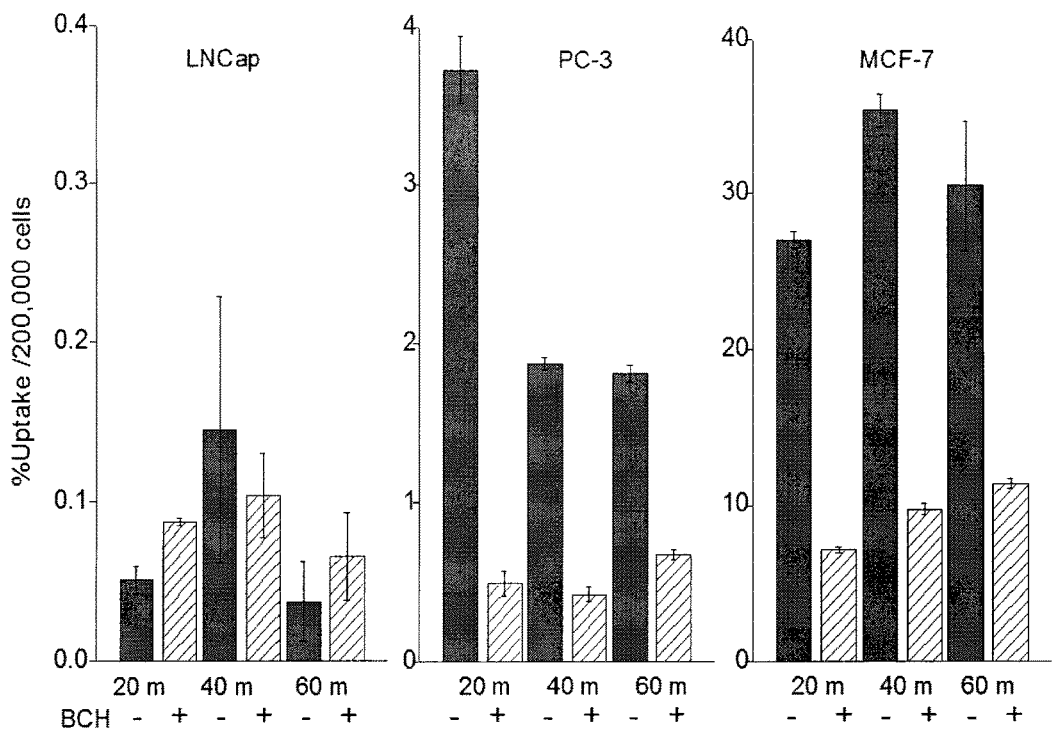
FIG. 35: Results of a non-competitive cell uptake study for exemplary compound 4-[$^{18}$F]FL in LNCaP, PC-3, and MCF-7 cells.

FIG. 35 depicts the results of a non-competitive cell uptake study for 4-[$^{18}$F]FL in LNCaP, PC-3, and MCF-7 cells at 20, 40 and 60 min in the presence (+) and absence (−) of the LAT-1 inhibitor BCH (10 mM). 74 kBq was added to each well, and tracer uptake was normalized to cell number.

Figure 36:
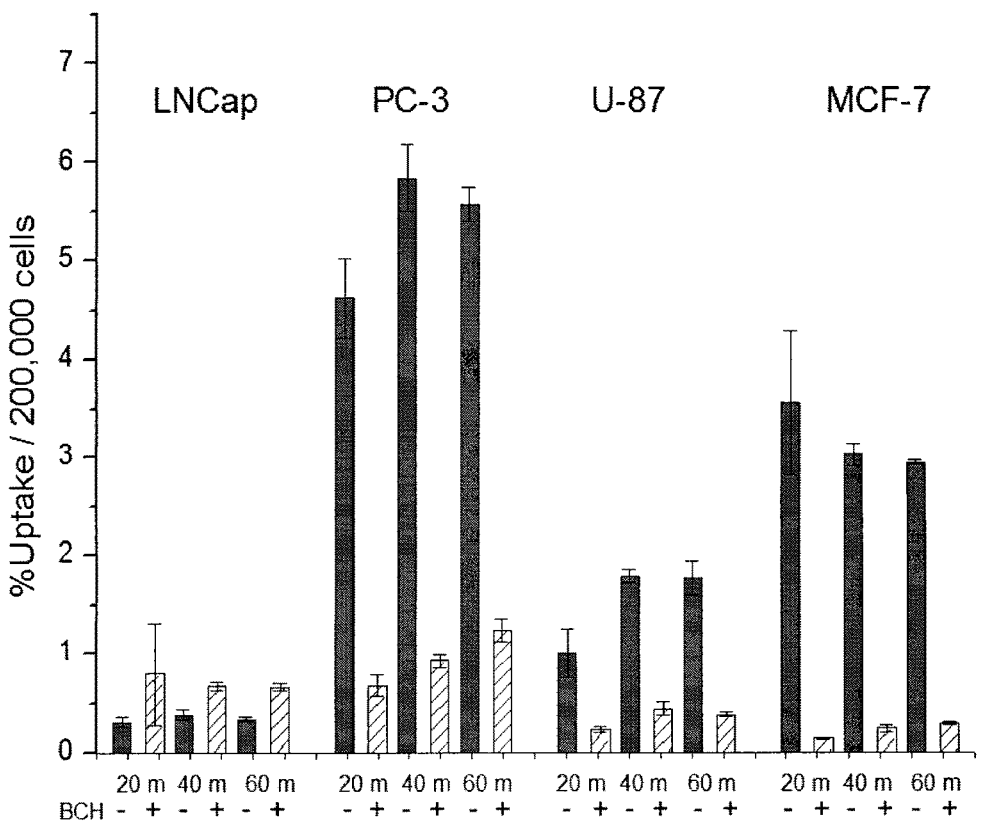
FIG. 36: Results of a non-competitive cell uptake study for exemplary compound 5-[$^{18}$F]FHL in LNCaP, PC-3, U-87 and MCF-7 cells.

FIG. 36 depicts results of a non-competitive cell uptake study for 5-[$^{18}$F]FHL (9) in LNCaP, PC-3, U-87 and MCF-7 cells at 20, 40 and 60 min in the presence (+) and absence (−) of the LAT-1 inhibitor BCH (10 mM). 74 kBq was added to each well, and tracer uptake was normalized to cell number.

Figure 37:
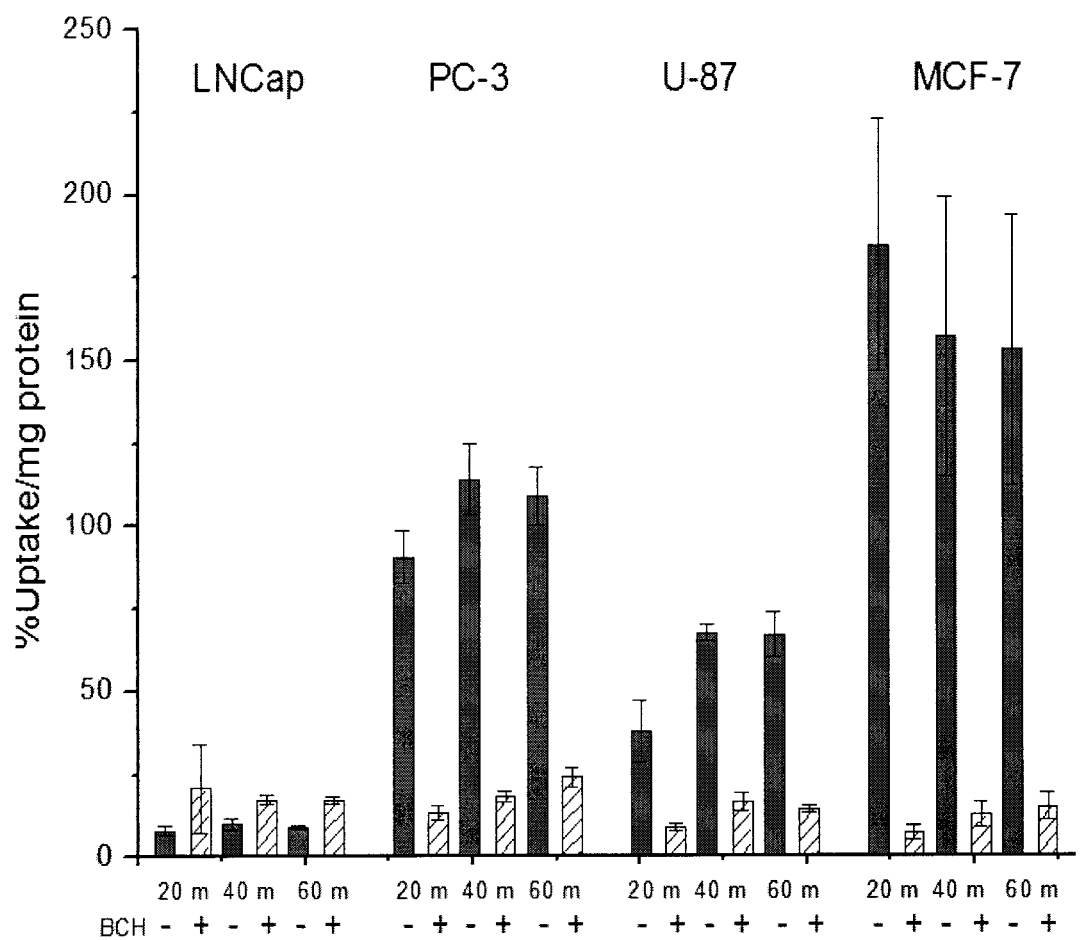
FIG. 37: Results of a non-competitive cell uptake study for exemplary compound 5-[$^{18}$F]FHL in LNCaP, PC-3, U-87 and MCF-7 cells).

FIG. 37 depicts results of a non-competitive cell uptake study for 5-[$^{18}$F]FHL (9) in LNCaP, PC-3, U-87 and MCF-7 cells at 20, 40 and 60 min in the presence (+) and absence (−) of the LAT-1 inhibitor BCH (10 mM). 74 kBq was added to each well, and tracer uptake was normalized to protein content.

In order to delineate the family of amino acid transporters responsible for the import of the above $^{18}$F amino acids into cells, a competitive assay was conducted, wherein a series of amino acids with known transporter preferences were applied to PC3 cells in large molar excess to the $^{18}$F amino acids to be tested. Since the blocking amino acids have known transporter preference, and are present in excess, they were expected to antagonize the uptake of the $^{18}$F amino acids if they share the same transporter preference.

Figure 38:
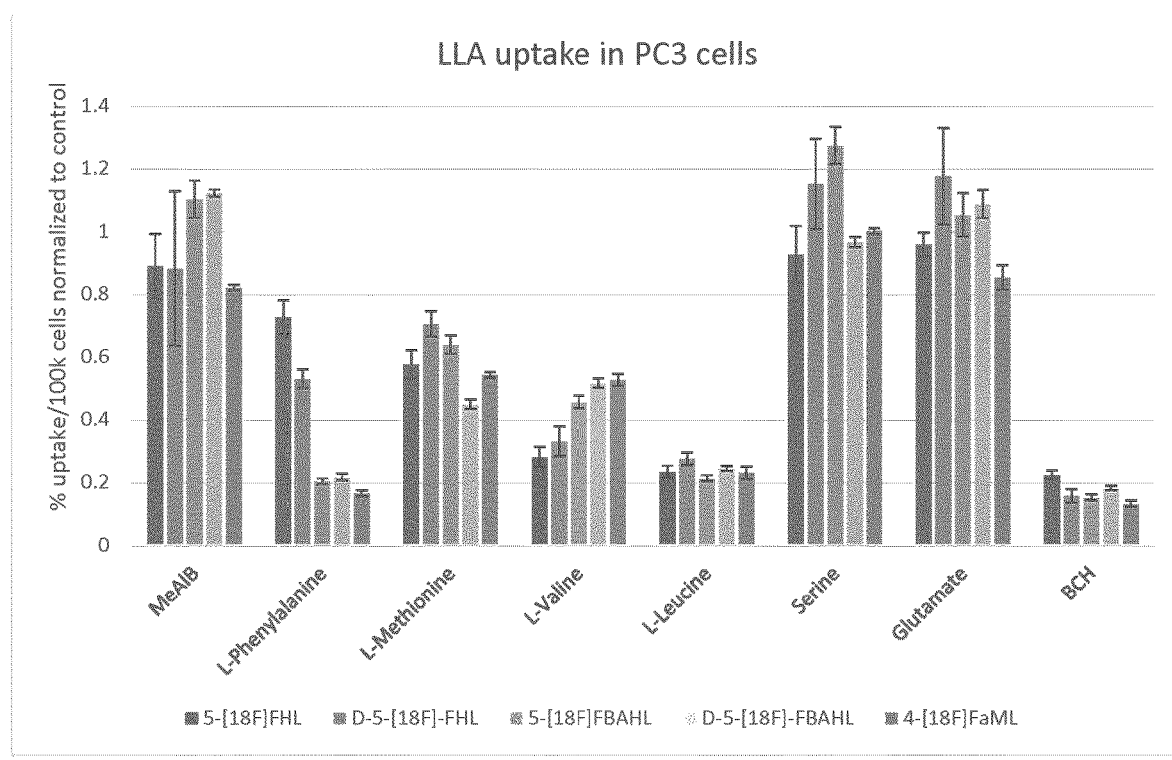
FIG. 38: Results of a competitive cell uptake study for exemplary compounds 5-[$^{18}$F]FHL, D-5-[$^{18}$F]-FHL, 5-[$^{18}$F]FBAHL, D-5-[$^{18}$F]-FBAHL, and 4-[$^{18}$F]FaML.

FIG. 38 depicts the results of such a competitive cell uptake study for 5-[$^{18}$F]FHL, D-5-[$^{18}$F]FHL, 5-[$^{18}$F]FBAHL, D-5-[$^{18}$F]FBAHL and 4-[$^{18}$F]FaM. Blocking compound amino acid transporter specificity: MeAIB=Type A, and PAT; L-Phe=Type L, and B°; L-Met=Type L and ASC2; L-Val=Type L, and ASC1; L-Leu=Type L; L-Ser=Type A and ASC; L-Glu=EAAT, Glu; BCH=Type L.

Example 24: Biodistribution Studies

All animal experiments were conducted in accordance with the guidelines established by the Canadian Council on Animal Care and approved by the Animal Care Committee of the University of British Columbia. In vivo biodistribution studies were performed in healthy mice (n=4 each) to evaluate normal organ uptake of 4-[18F]F. 5-[$^{18}$F]FHL and 5-[$^{18}$F]FBAHL. Biodistribution studies were also obtained in immunocompromized mice (NOD.Cg-Rag1$^{tm1Mom}$ Il2rg$^{tm1Wjl}$/SzJ) bearing human glioma (U-87, obtained from ATCC) or prostate cancer cell lines (PC-3) to evaluate tumor accumulation of 5-[$^{18}$F]FHL. For tumor bearing mice, 5×10$^6$ cells were injected subcutaneously in the dorsal flank of the mice. The tumors were grown to a diameter of approximately 5-7 mm prior to the biodistribution study. The animals were lightly sedated with isoflurane, and 1-2 MBq of $^{18}$F-labeled radiotracer was administered intravenously via the caudal lateral tail vein. The radioactivity in the syringe was measured before and after injection to ensure accurate determination of the amount injected. The animals quickly recovered from sedation and were allowed to roam free in the cage during the uptake period. At 15 (U-87 tumors, n=3) and 60 minutes (U-87, n=4 and PC-3, n=5), the animals were sedated with isoflurane, sacrificed by CO$_2$ asphyxiation and their blood was collected by cardiac puncture. The organs were harvested, rinsed with saline, blotted dry, and weighed. Radioactivity in each organ was measured using a PerkinElmer Wizard 2480 gamma counter, calibrated using a standard curve of $^{18}$F. Organ uptake data is reported as the percentage of injected dose per gram of tissue (% ID/g).

Figure 39:
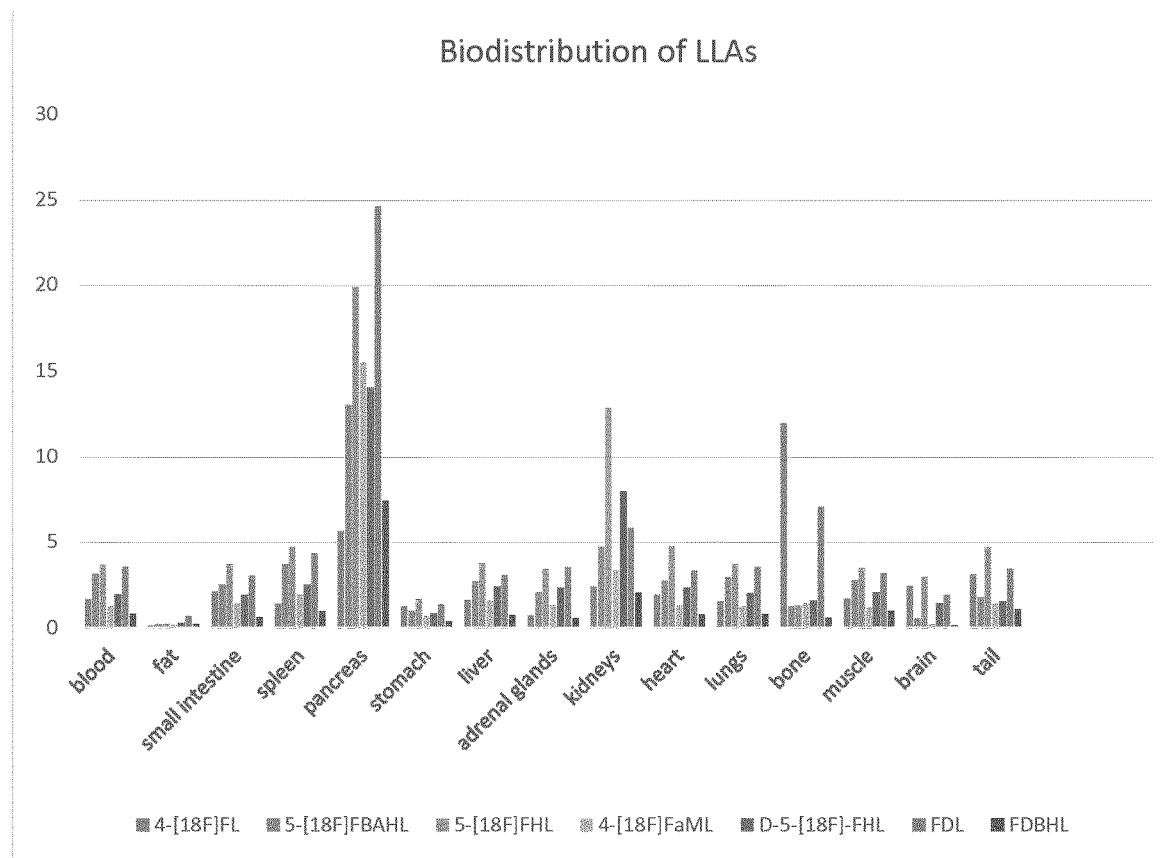
FIG. 39: Results of a biodistribution study of exemplary compounds 4-[$^{18}$F]FL, 5-[$^{18}$F]FBAHL, 5-[$^{18}$F]FHL, and 4-[$^{18}$F]FaML, D-5-[$^{18}$F]-FHL, FDL and FDBHL in selected organs.

FIG. 39 depicts the results of a biodistribution study of 4-[$^{18}$F]FL, 5-[$^{18}$F]FBAHL, 5-[$^{18}$F]FHL, 4-[$^{18}$F]FaML, D-5-[$^{18}$F]FHL, FDL and FDBHL in selected organs.

Figure 40:
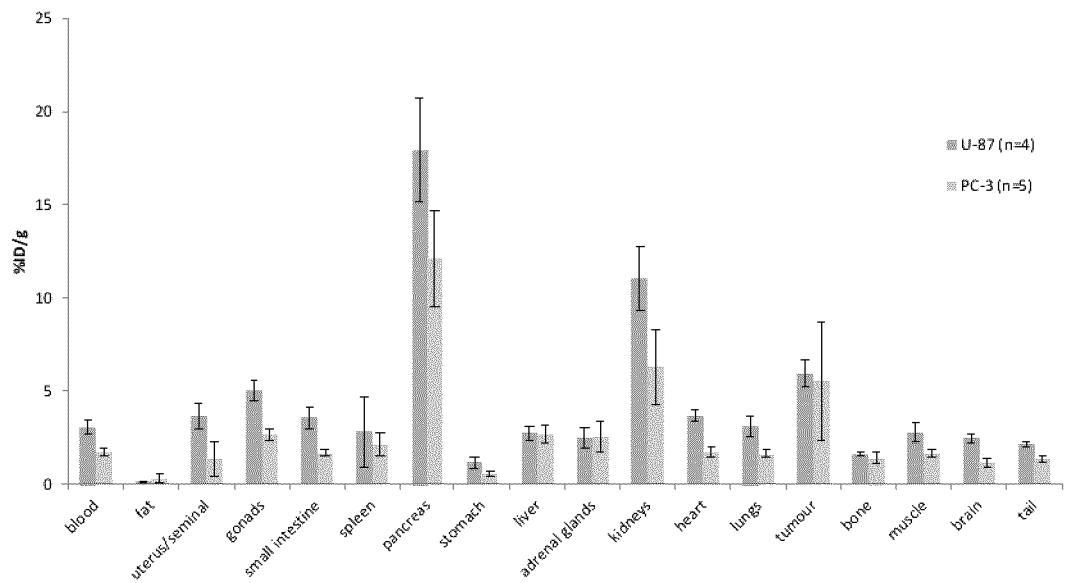
FIG. 40: Results of a biodistribution study of exemplary compounds 5-[$^{18}$F]FHL in selected organs at 1 h post injection in NRG mice bearing U-87 and PC-3 xenograft tumors.

FIG. 40 depicts the results of a biodistribution study of 5-[$^{18}$F]FHL in selected organs at 1 h post injection in NRG mice bearing U-87 (left bars) and PC-3 (right bars) xenograft tumors.

Figure 41:
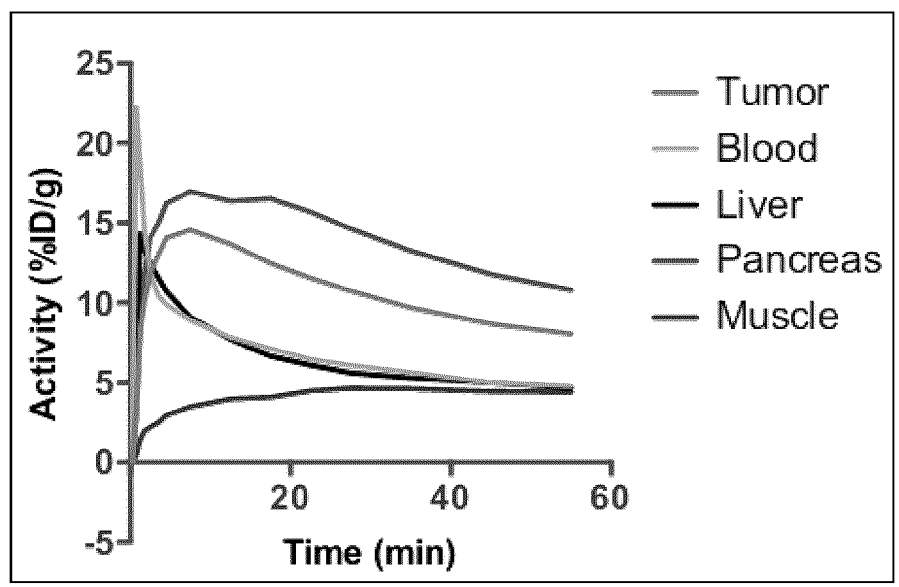
FIG. 41: Time-activity curves of the accumulation of 5-[$^{18}$F]FHL in selected organs.

FIG. 41 depicts the time-activity curves of the accumulation of 5-[$^{18}$F]FHL in selected organs, showing rapid accumulation in the U-87 tumor and pancreas peaking shortly before 10 minutes, followed by a slow progressive efflux of the amino acid.

Example 24: PET/CT Imaging

Dynamic PET/CT acquisitions were performed in a distinct set of mice to obtain representative images and follow the kinetics of uptake in normal organs (4-[$^{18}$F]FL) as well as normal organs and tumors (5-[$^{18}$F]FHL). The mice were sedated with isoflurane inhalation, a catheter was placed in the caudal lateral tail vein, and the mice were placed in a preclinical PET/CT scanner (Siemens Inveon). A low-dose CT scan was performed using 40 kV X-rays at 500 µA. Following CT imaging, the list-mode dynamic acquisition was started, and the radiotracer was injected (3.2-3.4 MBq). Dynamic scanning was continued for 60 minutes. In addition to dynamic images, static images were reconstructed at 50-60 minutes using an iterative reconstruction algorithm (3D-OSEM/MAP).

Figure 42:
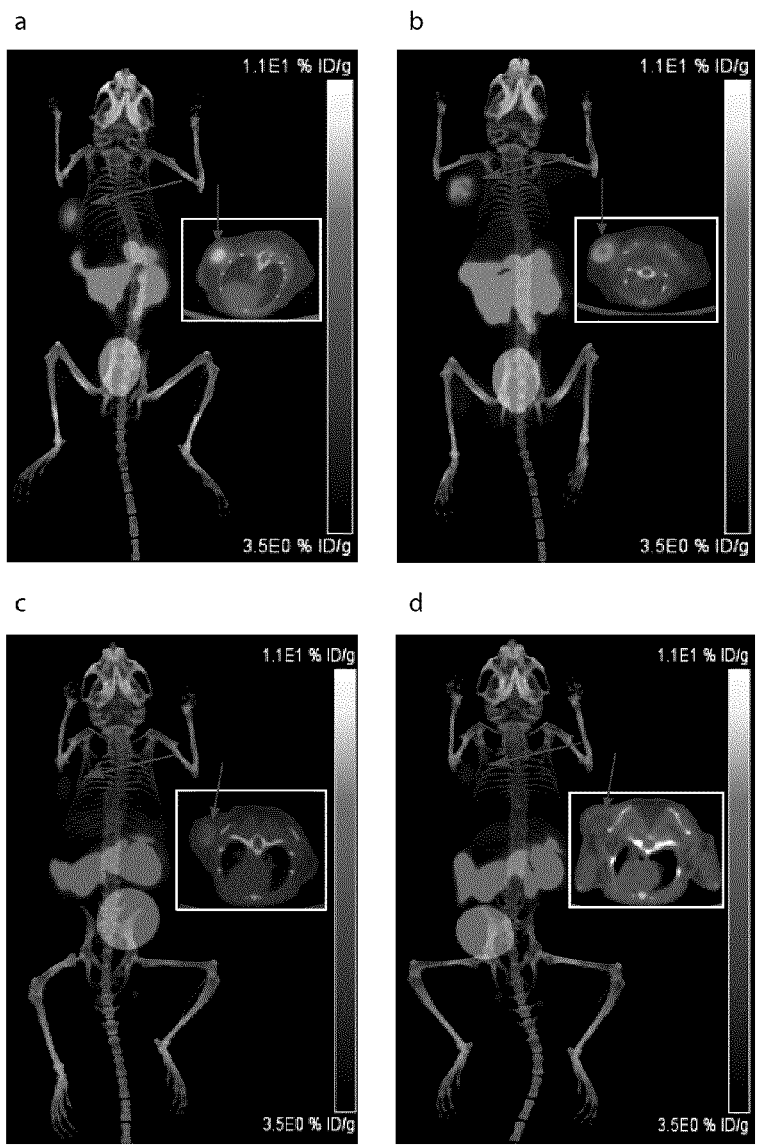
FIG. 42: Results of Xenograft imaging.

FIG. 42 depicts xenograft images, wherein whole-body maximum intensity projection images overlaid on CT of the biodistribution of 5-[$^{18}$F]FHL at 50-60 minutes for the U-87 tumor xenografts (a and b) and for the PC-3 tumor xenografts (c and d). Cross sectional images are shown in the insets. Each image represents an individual mouse, and an arrow indicates tumor position.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The invention claimed is:

1. A compound having a formula (I):

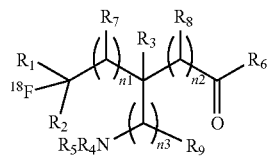

or a salt thereof or a stereoisomer thereof, wherein:

$n_1$ is 2, 3, 4 or 5;

$n_2$ and $n_3$ are 0;

$R_1$ is alkyl;

$R_2$ is alkyl;

$R_3$ is H;

$R_4$ is H or $COR_{10}$, wherein $R_{10}$ is an amino acid residue or peptide;

$R_5$ is H or $COR_{10}$, wherein $R_{10}$ is an amino acid residue or peptide;

$R_6$ is —OH; and $R_7$ is H.

2. The compound according to claim 1, wherein $n_1$ is 2.

3. The compound according to claim 1, wherein $n_1$ is 3.

4. The compound according to claim 1, wherein $R_1$ and $R_2$ are methyl.

5. The compound according to claim 1, wherein $R_4$ and $R_5$ are both H.

6. The compound according to claim 1, wherein one of $R_4$ and $R_5$ is H, and the other is $COR_{10}$.

7. The compound according to claim 1, wherein the amino acid residue is an amino acid selected from the group consisting of lysine (K), aspargine (N), glycine (G), alanine (A), glutamic acid (E), phenylalanine (F), histidine (H), and aspartic acid (D).

8. The compound according to claim 1, wherein the peptide comprises two or more amino acids selected from the group consisting of lysine (K), aspargine (N), glycine (G), alanine (A), glutamic acid (E), phenylalanine (F), histidine (H), and aspartic acid (D).

9. The compound according to claim 1, wherein the amino acid residue is glutamic acid (E).

10. A compound of claim 1, which is:

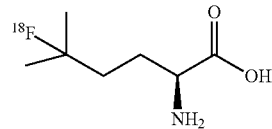

7

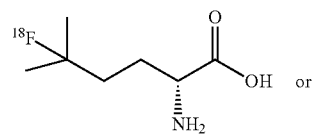

8 or

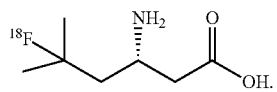

9

11. A $^{18}$F-labeled compound, which is:

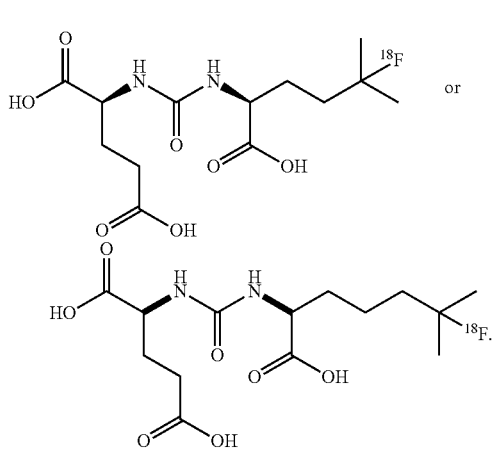

or

12. A method of PET imaging comprising administering a compound of claim 1 to a subject.

13. A method of diagnosis of a proliferative disease comprising administering a compound of claim 1 to a subject.

14. A compound of claim 1, which is:

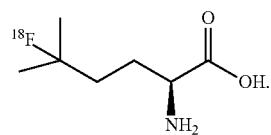

15. A method of PET imaging comprising administering a compound of claim 10 to a subject.

16. A method of diagnosis of a proliferative disease comprising administering a compound of claim 10 to a subject.

17. A method of PET imaging comprising administering a compound of claim 11 to a subject.

18. A method of diagnosis of a proliferative disease comprising administering a compound of claim 11 to a subject.

19. A method of PET imaging comprising administering a compound of claim 14 to a subject.

20. A method of diagnosis of a proliferative disease comprising administering a compound of claim 14 to a subject.

* * * * *